(12) United States Patent
Fleming et al.

(10) Patent No.: US 8,895,502 B2
(45) Date of Patent: Nov. 25, 2014

(54) β2-GLYCOPROTEIN I PEPTIDE INHIBITORS

(71) Applicant: Kansas State University Research Foundation, Manhattan, KS (US)

(72) Inventors: Sherry Fleming, Manhattan, KS (US); John M. Tomich, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 13/782,881

(22) Filed: Mar. 1, 2013

(65) Prior Publication Data

US 2013/0165391 A1  Jun. 27, 2013

Related U.S. Application Data

(63) Continuation-in-part of application No. PCT/US2011/049951, filed on Aug. 31, 2011.

(60) Provisional application No. 61/379,257, filed on Sep. 1, 2010.

(51) Int. Cl.

| *A61K 38/17* | (2006.01) |
|---|---|
| *A61K 39/395* | (2006.01) |
| *A61K 45/06* | (2006.01) |
| *C07K 14/47* | (2006.01) |
| *A61K 49/00* | (2006.01) |
| *C07K 14/16* | (2006.01) |

(52) U.S. Cl.
CPC ............. *C07K 14/47* (2013.01); *A61K 38/1709* (2013.01); *A61K 39/395* (2013.01); *A61K 45/06* (2013.01)
USPC .......................................................... 514/4.2

(58) Field of Classification Search
None
See application file for complete search history.

(56) References Cited

U.S. PATENT DOCUMENTS

| 5,877,278 | A |  | 3/1999 | Zuckermann et al. |  |
|---|---|---|---|---|---|
| 5,980,895 | A |  | 11/1999 | Pastan et al. |  |
| 7,642,234 | B2 |  | 1/2010 | Schroit et al. |  |
| 2003/0219406 | A1 |  | 11/2003 | Schroit et al. |  |
| 2006/0228299 | A1 | * | 10/2006 | Thorpe et al. | ................ 424/1.49 |
| 2007/0083334 | A1 | * | 4/2007 | Mintz et al. | ..................... 702/19 |
| 2009/0068207 | A1 |  | 3/2009 | Breitbart et al. |  |

OTHER PUBLICATIONS

Accession No. Q6LAL7, accessed Apr. 29, 2014 at URL: http://www.uniprot.org/uniprot/Q6LAL7.*
UnitProtKB Accession No. Q6LAL7 accessed Aug. 25, 2014 at URL: uniprot.org/uniprot/Q6LAL7.*
UnitProtKB Accession No. Q1ILL7 (accessed Aug. 25, 2014 at URL: uniprot.org/uniprot/Q1ILL7).*
UnitProtKB Accession No. Q5E8J4 (accessed Aug. 25, 2014 at URL: uniprot.org/uniprot/Q5E8J4).*
UnitProtKB Accession No. B4DPN0 (accessed Aug. 25, 2014 at URL: uniprot.org/uniprot/B4DPN0).*
Arumagam, Thiruma V. "Complement Mediators in Ischemia-Reperfusion Injury" Science Direct, 2006.
Fleming, Sherry D. "Complement Component C5a Mediates Hemorrhage-Induced Intestinal Damage," Journal of Surgical Research, 2008.
Fleming, Sherry D. "Mice Deficient in Complement Receptors 1 and 2 Lack a Tissue Injury-Inducing Subset of the Natural Antibody Repertoire," The Journal of Immunology, 2002.
Fleming, Sherry D. "Anti-Phospholipid Antibodies Restore Mesenteric Ischemia/Reperfusion-Induced Injury in Complement Receptor 2/Complement Receptor 1-Deficient Mice," The Journal of Immunology, 2004.
Zhang, Ming, "Identification of the Target Self-Antigens in Reperfusion Injury," The Journal of Experimental Medicine, Jan. 3, 2006.
Chan, Rodney K. "Attenuation of Skeletal Muscle Reperfusion Injury With Intravenous 12 Amino Acid Peptides that bind to pathogenic IgM," Surgery, vol. 139, No. 2, May 28, 2005.
Banerjee, Subhasis, "Mouse Models for Preeclamsia: Disruption of Redox-Regulated Singaling," Resproductive Biology and Endocrinology, Jan. 15, 2009.
Cavazzana, Anna, "An Analysis of Experimental Conditions Influencing the Anti-Beta2-Glycoprotein I ELISA Assay Results," Ann. N.Y. Acad. Sci. 1109; 484-492; 2007.
Cockrell, E. "Annexin A2: Biology and Relevance to the Antiphospholipid Syndrome," Lupus, vol. 17, 2008, 943-951.
Conti, F. "Beta-2-Glycoprotein I Expression on Monocytes is Increased in Anti-Phospholipid Antibody Syndrome and Correlates with Tissue Factor Expression," Clin. Exp. Immunol. vol. 132, 509-516, 2003.
Henrnandez, Lucrecia, "Role of Neutrophils in Ischemia-Reperfusion-Induced Microvascular Injury," The American Physiological Society, 1987.
Alard, Jean-Eric, "TLR2 Is One of the Endothelial Receptors for Beta2-Glycoprotein I," Journal of Immunology, Jul. 2, 2010.
Arumugam, Thiruma, "Toll-Like Receptors in Ischemia-Reperfusion Injury," Shock, vol. 32, No. 1, 4-16, 2009.
Costa, Cristina, "Role of Component C5 in Cerebral Ischemia/Reperfusion Injury," Brain Research, 1100(1), 142-151, Jul. 19, 2006.
De Zwaan, Chris, "Prevention of Cardiac Cell Injury During Acute Myocardial Infarction," Am J. Cardiovasc Drugs vol. 3(4) 245-251; 2003.
Fleming, Sherry D., "Complement Inhibitors in Rheumatic Diseases," Modern Therapeutics in Rheumatic Diseases, Human Press, Inc. 2002.
Fleming, Sherry D., "Heat Stress Protection Against Mesenteric I/R-Induced Alterations in Intestinal Mucosa in Rats," J. Appl. Physiol vol. 92, 2600-2607; Mar. 26, 2008.
Fleming, Sherry D., "Domain V Peptides Inhibit Beta2-Glycoprotein I-Mediated Mesenteric Ischemia/Reperfusion-Induced Tissue Damage and Inflammation," The Journal of Immunology, Dec. 14, 2010.
Fleming, Sherry D., "Accelerated Ischemia/Reperfusion-Induced Injury in Autoimmunity-Prone Mice," The Journal of Immunology, 2004.

(Continued)

*Primary Examiner* — Christina Bradley
*Assistant Examiner* — Kristina M Hellman
(74) *Attorney, Agent, or Firm* — Hovey Williams LLP

(57) ABSTRACT

Therapeutic peptides (and peptoids) for preventing or inhibiting tissue damage associated with ischemia and/or reperfusion are provided, along with peptides (and peptoids) for preventing or inhibiting cancerous tissue growth. The peptides are derived from β2-glycoprotein I. Pharmaceutical and veterinary compositions comprising the peptides are also provided. Methods of using the peptides to prevent or inhibit tissue damage associated with ischemia and/or reperfusion and/or to prevent or inhibit tissue damage or the growth of cancerous tissue are also provided.

10 Claims, 23 Drawing Sheets
(8 of 23 Drawing Sheet(s) Filed in Color)

(56) References Cited

OTHER PUBLICATIONS

Fruchterman, Todd M. "Complement Inhibition Prevents Gut Ischemia and Endothelial Cell Dysfunction after Hemorrhage/Resuscitation," Surgery, vol. 124, No. 4, Oct. 1998.
Gries, Anni, "Characterization of Isoelectric Subspecies of Asialo-Beta2-Glycoprotein I," Biochem. J. vol. 260, 531-534; 1989.
Hoffman, Sara M., "Helicobacter Infection Alters MyD88 and Trif Signalling in Response to Intestinal Ischaemia-Reperfusion," Experimental Physiology, 1-10; 2010.
Hylton, Dianah J., "Hemorrhage-Induced Intestinal Damage is Complement-Independent in Helicobacter Hepaticus-Infected Mice," Shock, vol. 34, No. 5, 467-474; 2010.
Hylton, Diana J., "Macrophage-Produced IL-12p70 Mediates Hemorrhage-Induced Damage in a Complement-dependent Manner," Shock, vol. 35, No. 2, 134-140, 2011.
Iwamoto, Takeo, "Chemical Synthesis and Characterization of Peptides and Oligomeric Proteins Designed to Form Transmembrane Ion Channels," Int. J. Peptide Protein Res. 43, 597-607, 1994.
Kulik, Liydmila, "Pathogenic Natural Antibodies Recognizing Annexin IV Are Required to Develop Intestinal Ischemia-Reperfusion Injury," The Journal of Immunology, vol. 182, 5363-5373; Jan. 24, 2010.
Lee, Haekyung, "Early Complement Factors in the Local Tissue Immunocomplex Generated During Intestinal Ischemia/Reperfusion Injury," Molecular Immunology vol. 47, 972-981; 2010.
Monestier, Marc, "Monoclonal Antibodies from NZW x BXSB F1 Mice to Beta2-Glycoprotein I and Cardiolipin," The Journal of Immunology, vol. 156, 2631-2641; 1996.
Moltalvo, Vanessa, "Complement Deposits on Ocular Tissues Adjacent to Sites of Inflammation," Current Eye Research, vol. 32, 917-322, 2007.
Moses, Tiffany, "TLR4-Mediated Cox-2 Expression Increases Intestinal Ischemia/Reperfusion-Induced Damage," Journal of Leukocyte Biology, vol. 86, Oct. 2009.
Passam, F.H. "In Vivo Modulation of Angiogenesis by Beta 2 Glycoprotein I" Journal of Autoimmunity, 1-9, 2010.
Pope, Michael R.., "Complement Regulates TLR4-Mediated Inflammatory Responses During Intestinal Ischemia Reperfusion," Molecular Immunology, 2010.
Pope, Michael R., "Small Beta2-Glycoprotein I Peptides Protect from Intestinal Ischemia Reperfusion Injury," Journal of Immunology, Oct. 2012.
Rajnik, Michael, "Induction of Early Inflammatory Gene Expression in a Murine Model of Nonresuscitated, Fix-volume Hemorrhage," Shock, vol. 17, No. 4, 322-328, 2002.
Szebeni, Janos, "Complement Activation During Hemorrhagic Shock and Resuscitation in Swine," Shock, vol. 20, No. 4, 347-355, 2003.
Tomasi, Maurizio, "Human Beta2-Glycoprotein I attenuates Mouse Intestinal Ischemia/Reperfusion Induced Injury and Inflammation," Molecular Immunology, vol. 52, 207-216, Jun. 27, 2012.
Wong, R.C.W. "Consensus Guidelines on Anti-Beta 2 Glycoprotein I Testing and Reporting," Pathology vol. 40 (1) 58-69, Jan. 2008.
Zhou, H., "Toll-Like Receptor (TLR)-4 Mediates Anti-Beta2 GPI/Beta2GPI-Induced Tissue Factor Expression in THP-1 Cells," Clinical & Experimental Immunology, The Journal of Translation Immunology, vol. 169, 189-198, 2010.
International Search Report and Written Opinion dated Mar. 8, 2012 in the corresponding PCT/US11/49951 application filed Aug. 31, 2011.

* cited by examiner

```
        281         291         301         311       317
296 H-IHFYCKNKEKKCSYTVEAHCRDGTI-OH   (SEQ ID NO:9)
305          KKCSYTVEAHCRDGTIEIPSCFKEHS-OH (SEQ ID NO:10)
322                      IPSCFKEHSSLAFWKTDASELTPC
                                          (SEQ ID NO:18)
```

A. B6 Sham 
B. Sham+Peptide 
C. B6 IR 
D. B6 IR+β$_2$GPI 100 
E. B6 IR+β$_2$GPI 181 
F. B6 IR+β$_2$GPI 296 
G. B6 IR+β$_2$GPI 296C-S 
H. B6 IR+β$_2$GPI 305 
I. B6 IR+β$_2$GPI 322

β2-GLYCOPROTEIN I PEPTIDE INHIBITORS

CROSS-REFERENCE TO RELATED APPLICATIONS

The present application is a continuation-in-part of International Application Serial No. PCT/US2011/049951, filed Aug. 31, 2011, which claims the priority benefit of U.S. Provisional Patent Application Ser. No. 61/379,257, filed Sep. 1, 2010, both entitled β2-GLYCOPROTEIN I PEPTIDE INHIBITORS, and hereby incorporated by reference herein in their entireties.

FEDERALLY SPONSORED RESEARCH OR DEVELOPMENT

This invention was made with government support under Contract Nos. R01AI061691, P20 RR017686, and RR016475 awarded by the National Institute of Health (NIH). The United States government has certain rights in the invention.

SEQUENCE LISTING

The following application contains a sequence listing in computer readable format (CRF), submitted as a text file in ASCII format entitled "SequenceListing.txt," created on Feb. 19, 2013, as 13 KB. The content of the CRF is hereby incorporated by reference.

BACKGROUND OF THE INVENTION

1. Field of the Invention

The present invention relates to peptide and/or peptoid inhibitors derived from β2-glycoprotein I ("β2-GPI") that can be used to prevent or inhibit damage from ischemia and reperfusion in various diseases and conditions.

2. Description of Related Art

A lack of blood flow (ischemia) and therefore lack of oxygen (hypoxia) to cells and organs results in cellular death and tissue damage; however, the return of blood flow (reperfusion) to the cell or organ significantly magnifies the tissue damage initiated by ischemia. Reperfusion injury of one tissue or organ may also result in tissue damage in other organs, sometimes resulting in multiple organ failure. Reperfusion injury was first identified as a critical care issue during the Vietnam conflict. Soldiers who had been shot in the abdomen survived their wounds and avoided sepsis, but eventually died on Days 5-7 due to pulmonary complications. Since this time, research has shown that the pulmonary complications were due to an excessive immune response in the intestine which sends the inflammatory cells to other mucosal organs, primarily the lungs. As the mortality rate for mesenteric ischemia/ reperfusion ("IR") remains at 70-90% today, therapeutic development for this ailment is desperately needed.

Numerous other clinical conditions result in IR-induced injury ranging from myocardial infarction, cardiac bypass surgery, stroke, and organ transplantation. In addition, hemorrhage, heat shock, and burns frequently lead to decreased blood flow to the non-vital intestine. These clinical conditions are significant, as approximately 15,000 transplants and 30,000 cases of intestinal IR (mortality rate of 60-80%) occur each year in the United States. In addition, myocardial infarction and stroke are two of the leading causes of death in the U.S.

In the last two decades, the complement system of the innate immune response has been identified as the blood component responsible for such tissue damage. Although a number of existing complement inhibitors have been shown to provide effective therapy in several animal models, there is no approved drug for treating mesenteric ischemia/reperfusion or multiple organ failure in humans or other mammals. Research therapeutics for mesenteric IR include complement inhibitors and peptides to non-muscle myosin. Complement inhibitors prevent a broad spectrum of the innate immune response, but can only be used short-term, as the decrease in immune response also renders the patient unable to respond to bacteria, which can be particularly dangerous in treating intestinal damage where translocation of bacteria is highly likely. Non-muscle myosin peptides only recognize intracellular components, which means that the cellular injury must have already begun. In addition, there is limited evidence that the inflammatory response is actually attenuated.

Seminal studies on IR have determined that during reperfusion, complement activation is initiated by naturally occurring antibody (NAb) recognition of newly expressed antigens (neoantigens). Produced by peritoneal B1a B cells, IgM and IgG3 NAbs recognize multiple phospholipid binding proteins including the serum protein, β2-glycoprotein I ("β2-GPI"). β2-GPI, also known as apolipoprotein H, is a member of the complement control protein family but does not exhibit any known complement regulating function. As used herein, references to β2-GPI are intended to include apolipoprotein H. With five complement regulatory domains, β2-GPI exists in several conformations that are stabilized by carbohydrate moieties. Each conformation is proposed to have distinct biological activity. After binding anionic phospholipids, β2-GPI undergoes conformational changes allowing NAb recognition and binding of β2-GPI. However, β2-GPI is also a cofactor for plasminogen activation and an opsonin for the clearance of apoptotic cells by phagocytes. By binding to anionic phospholipids, DNA or other negatively charged molecules, β2-GPI is a major antigenic target for anti-phospholipid antibodies found in the serum of anti-phospholipid antibody syndrome (APLS) and systemic lupus erythematosus patients. Accordingly, increased anti-β2-GPI antibody titers correlate with increased risk of ischemic stroke or heart disease in APLS or systemic lupus erythematosus patients, respectively.

Our previous work demonstrated that during reperfusion β2-GPI binds to ischemic cell membranes allowing antibody recognition necessary for complement activation and inflammation. Using an in vitro model, anti-β2-GPI antibodies recognized β2-GPI bound to the surface of hypoxic endothelial cells, and β2-GPI binding to damaged ischemic intestinal tissue correlated with tissue injury (Fleming, S. D. et al., *J. Immunol.* 185:6168-6178 (2010)). As discussed in more detail below, it has been found that peptides derived from β2-GPI sequence attenuated intestinal damage and inflammation. Recent evidence also indicates that the mechanism of tissue injury is similar between reperfusion damage in the intestine, liver, and lungs, suggesting that the peptides may be useful therapeutics for these tissues as well.

Additionally, it has also been found that β2-GPI peptides may be of therapeutic value in chronic ischemic conditions. One prominent example of chronic ischemia occurs in cancerous tumors. As cancer progresses, the tumor becomes invasive leading to metastasis. Hypoxia plays a major role in tumor metastasis. It affects not only the autonomous tumor cell functions like cell division and invasion, which play a role in genetic instability and therapy resistance, but also the non-autonomous processes like angiogenesis, lymphangiogenesis, and inflammation, which all contribute to metastasis.

Such malignant tumors account for about 12% of all deaths worldwide. During metastasis, changes occur within the tumor and in the surrounding tissue promoting additional cancer progression. The internal tumor changes include genetic, epigenetic and metabolic transformation, while externally, the microenvironment undergoes a significant modification. Specifically, the microenvironment becomes acidic, hypoxic, and inflamed leading to angiogenesis (formation of new blood vessels) and increased microparticle shedding into the blood stream. Tumor growth requires angiogenesis, which is the formation of new blood vessels. Angiogenesis provides oxygen and nutrients to growing tumor cells and is induced by a number of factors including endoglin and vascular endothelial growth factor (VEGF). In the present work, we hypothesized that β2-GPI-derived peptides may attenuate angiogenesis and tumor growth.

SUMMARY OF THE INVENTION

The present invention is broadly concerned with prophylactic and/or therapeutic β2-GPI-derived peptides (and peptoids) for preventing or inhibiting tissue damage and inflammation caused by ischemia and/or reperfusion, and/or for preventing or inhibiting the growth of cancerous tissue (e.g., tumor growth). The peptides comprise amino acid residues derived from the lipid-binding domain (V) of native mouse β2-GPI (SEQ ID NO. 14) or human β2-GPI (SEQ ID NO. 15), and preferably comprise cysteine to serine substitutions from the native mouse β2-GPI (SEQ ID NO. 14) or human β2-GPI (SEQ ID NO. 15) sequences from which they are derived.

In one or more embodiments, the peptides comprise amino acid residues selected from the group consisting of: IHFYX$^1$KNKEKKX$^1$SYTVEDAQX$^1$RDGTI, where each X$^1$ is C or S (SEQ ID NO. 1); KKX$^1$SYTVEDAQX$^1$RDGTIEX$^2$X$^3$X$^4$X$^1$FKEHS, where each X$^1$ is C or S, X$^2$ is I or V, X$^3$ is P or G, and X$^4$ is R or K (SEQ ID NO. 2); KKSSYTVEDAQS (SEQ ID NO. 3); residues 3-12 of SEQ ID NO. 3; residues 3-12 of SEQ ID NO. 3 with D-amino acids; SQADEVTYSS with D-amino acids (SEQ ID NO. 4); TEDAQX$^1$IDGTIEV, where each X$^1$ is C or S (SEQ ID NO. 5); X$^1$IDGTIEVX$^3$KX$^1$, where each X$^1$ is C or S, and X$^3$ P or G (SEQ ID NO. 6); KKX$^1$SYTEDAQX$^1$IDGTIEVPKX$^1$FKEHS, where each X$^1$ is C or S (SEQ ID NO. 7); VSFFX$^1$KNKEKKX$^1$SYTEDAQXper1IDGTI, where each X$^1$ is C or S (SEQ ID NO. 8); IHFYX$^1$KNKEKKX$^1$SYTVEAHX$^1$RDGTI, where each X$^1$ is C or S (SEQ ID NO. 9); KKCSYTVEAHCRDGTIEIPSCFKEHS (SEQ ID NO. 10); KKSSYTVEAHS (SEQ ID NO. 12); residues 3-11 of SEQ ID NO. 12; residues 3-11 of SEQ ID NO. 12 with D-amino acids; SHAEVTYSS with D-amino acids (SEQ ID NO. 13), KKSSYTVEAHSRDGTI (SEQ ID NO. 19), and conservatively modified sequence variants thereof.

In some embodiments, the peptides are actually peptoids comprising the above-referenced amino acid residues, or the conservatively modified variants thereof. In some embodiments, the peptoids comprise amino acid residues that are reversed sequences (i.e., in reversed sequence order) of the sequences listed above, or conservatively modified variants thereof.

A composition comprising one or more of the above-listed peptides and conservatively modified sequence variants thereof is also provided. The composition comprises the peptide(s) dissolved or dispersed in a pharmaceutically-acceptable carrier.

The invention is also concerned with a method of treating a condition associated with ischemia and/or reperfusion injury or preventing or inhibiting tissue damage caused by ischemia and/or reperfusion. The method comprises administering to a subject suffering from or about to undergo an ischemic event, a therapeutically-effective amount of one or more of the above-listed peptides, and conservatively modified sequence variants thereof. Advantageously, the peptides compete with serum protein β2-GPI in the subject and inhibit its binding to tissue, thereby preventing or inhibiting the injury or tissue damage.

A method of preventing or inhibiting growth of cancerous tissue is also provided. The method comprises administering to a subject a therapeutically-effective amount one or more of the above-listed peptides, and conservatively modified sequence variants thereof. Advantageously, the peptides slow the rate of the cancerous tissue growth.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figures 1A, 1B:
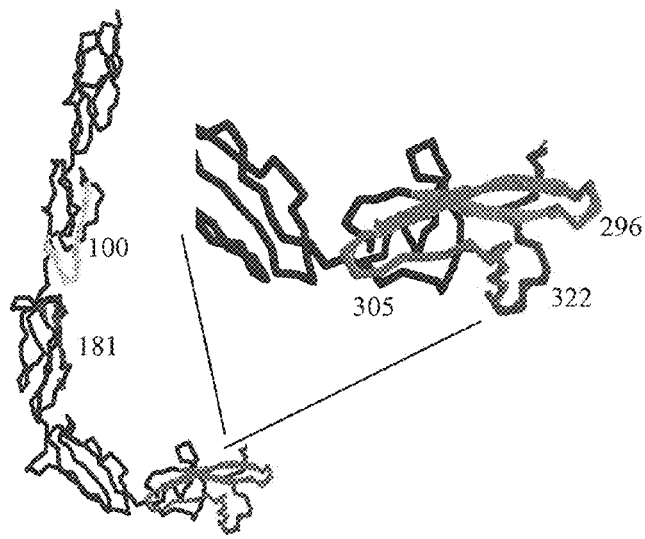
FIG. 1(A) is a ribbon diagram of human β2-GPI with peptide locations identified by color, as described in Example 1.
FIG. 1(B) shows the overlapping sequences of peptides p296, p305, and p322 from mouse β2-GPI in Example 1.

The present invention is concerned with therapeutic β2-GPI-derived peptides and peptoids for inhibiting and preventing tissue damage and inflammation related to ischemia and/or reperfusion. Unless the context otherwise dictates, the term "peptide," as used herein, encompasses both peptides and peptoids (discussed in more detail below). The term "derived" with respect to the sequences described herein, such as the inventive β2-GPI-derived peptides, means that the peptide sequences have been selected, designed, or synthesized based upon a wild type or naturally-occurring β2-GPI sequence, and can be identical thereto, or have one or more deletions, additions, and/or substitutions with natural or unnatural amino acids or peptidomimetics. It will be appreciated that suitable β2-GPI sequences may vary from species to species and the exact sequence of the therapeutic peptides will be dependent upon the particular sequence of the β2-GPI for the species to be treated (e.g., humans and non-human mammals such as mice, rats, dogs, cats, pigs, horses, cattle, etc.); although it has also been found that β2-GPI peptides (and in particular the whole β2-GPI protein) can be effective at preventing injury cross-species, as demonstrated in the Examples. In general, the peptides are derived from and preferably correspond to the lipid-binding domain (V) of β2-GPI. More preferably, the peptides comprise the phospholipid binding, lysine rich region and/or adjacent regions of serum protein β2-GPI for a given subject. For example, the peptides can be derived from any of these regions of native mouse β2-GPI (SEQ ID NO. 14) or human β2-GPI (SEQ ID NO. 15).

Preferred peptides will comprise (consist essentially, or even consist of) amino acid residues selected from the group consisting of: IHFYX$^1$KNKEKKX$^1$SYTVEDAQX$^1$RDGTI, where each X$^1$ is C or S (SEQ ID NO. 1); KKX$^1$SYTVEDAQX$^1$RDGTIEX$^2$X$^3$X$^4$X$^1$FKEHS, where each X$^1$ is C or S, X$^2$ is I or V, X$^3$ is P or G, and X$^4$ is R or K (SEQ ID NO. 2); KKSSYTVEDAQS (SEQ ID NO. 3); residues 3-12 of SEQ ID NO. 3; residues 3-12 of SEQ ID NO. 3 with D-amino acids; SQADEVTYSS with D-amino acids (SEQ ID NO. 4); TEDAQX$^1$IDGTIEV, where each X$^1$ is C or S (SEQ ID NO. 5); X$^1$IDGTIEVX$^3$KX$^1$, where each X$^1$ is C or S, and X$^3$ P or G (SEQ ID NO. 6); KKX$^1$SYTEDAQX$^1$IDGTIEVPKX$^1$FKEHS, where each X$^1$ is C or S (SEQ ID NO. 7); VSFFX$^1$KNKEKKX$^1$SYTEDAQX$^1$IDGTI, where each X$^1$ is C or S (SEQ ID NO. 8); IHFYX$^1$KNKEKKX$^1$SYTVEAHX$^1$RDGTI, where each X$^1$ is C or S (SEQ ID NO. 9); KKCSYTVEAHCRDGTIEIPSCFKEHS (SEQ ID NO. 10); KKSSYTVEAHS (SEQ ID NO. 12); residues 3-11 of SEQ ID NO. 12; residues 3-11 of SEQ ID NO. 12 with D-amino acids; SHAEVTYSS with D-amino acids (SEQ ID NO. 13), and/or KKSSYTVEAH-SRDGTI (SEQ ID NO. 19). In the foregoing sequences, it is particularly preferred that X$^1$ is S. In other words, in one or more embodiments, the sequences are preferably substantially free of cysteine residues. Combinations of two or more different β2-GPI-derived peptides can also be used in the various embodiments described herein.

Peptides for use in the invention can comprise (consist essentially or even consist of) amino acids identical to the above sequences, but can also include conservatively modified sequence variants thereof. As used herein, "conservatively modified sequence variants" refers to peptide sequences having a certain degree of homology (preferably greater than about 50%, more preferably greater than about 60%, and even more preferably greater than about 98%), which also retain the function of the original peptide or fragment (i.e., inhibition of tissue damage due to IR). SEQ NOs. 1-8 are particularly preferred for use in peptides intended for use in human treatment methods. It will be appreciated that when referring to amino acids that are present as part of a peptide, the amino acids are actually amino acid residues, regardless of whether "residues" is specifically stated herein.

The peptides can be synthesized using any suitable technique, including traditional solid-phase synthesis with 9-fluorenylmethoxycarbinyl (Fmoc) chemistry using Fmoc-protected amino acids, followed by lyophilization until use. The peptides can further comprise label, tag, or targeting moieties on either the C- or N-terminus, which can be attached using known methods. Labels and tags can be used to visualize, track, and/or identify the peptide after administration, while targeting moieties preferably localize in, and are selectively taken up by tissues, allowing the peptide to be selectively directed to the area of need. These moieties can also be utilized to modify properties of the peptides, such as solubility or detectability. Examples of moieties that can be attached to the peptides include affinity/epitope tags (e.g., FLAG, polyhistidine, etc.), biotin, fluorescent markers, stable or radioactive isotopes and isotope-labeled amino acids, sugars, polyethylene glycol (PEG), covalent crosslinking moieties (e.g., maleimides, aryl azides, N-hydroxy succinimide esters, etc.), toxins, lipids, and/or sterols.

As noted above, suitable inventive peptides for use in the invention can actually be "peptoids." Peptoids are oligo (N-substituted) amides (and preferably oligo (N-substituted) glycines). Peptoids can be synthesized using any suitable techniques, such as those described in the Examples below, as well as in U.S. Pat. No. 5,877,278, incorporated by reference herein. Peptoids differ from peptides in that they are not composed of naturally-occurring amino acids linked in peptide bonds, and do not have stereo centers. However, they may be designed to have structural features (e.g., reactive sites) which are closely related to naturally-occurring peptides and proteins, while being more resistant to enzymatic attack and degradation. Peptoids according to the invention will be derived from and have the same amino acid sequence(s) as described herein with respect to the disclosed inventive peptides, except that the amino acid side chain will be on the nitrogen in the peptoid rather than on the alpha carbon (as in the peptide backbone). By moving the side chain of the amino acid to the amide nitrogen, peptoids appear as a string of glycines with various substitutions on the nitrogen. Those skilled in the art will appreciate that in one or more embodiments, the peptoid sequences can also be in the reversed order to provide more proper orientation of the N-substituted R-groups, although the reversed sequence is not necessarily required for the peptoids to be effective (as indicated by the data in the working examples using D-amino acids). Regardless of these differences, the peptoids maintain the backbone of the peptide from which their sequence is derived.

Amphiphilic in nature, peptoids have unique folding patterns and are more membrane permeable than peptides. In previous work, these properties allowed for development of a peptoid that mimics lung surfactant B and is potentially useful in treating respiratory distress syndrome in newborns, as reported by Seurynck et al. (*Chem Biol.* 12(1):77-88 (2005)). In that work, the data indicated that surfactant B mimic (peptoid) maintained lipid membrane interactions similar to the natural substance. Therefore, the administration of β2-GPI-derived peptoids according to the invention should also compete with native β2-GPI for membrane binding in the same way as the β2-GPI-derived peptides described in the Examples. In addition, a recent study reported a peptoid which inhibits the interaction between the transcription factor, p53, and a negative regulator, human double minute 2 (hDM2) (Toshiaki et al., *J. Am. Chem. Soc.* 128 (6):1995-2004 (2006)). As approximately 50% of cancers contain a mutated p53, these data illustrate that peptoids in general may also be used as cancer therapeutics. As such, β2-GPI-derived peptoids according to the various embodiments of the invention may be equally useful as cancer therapeutics. Taken together, these data suggest that peptoids based on the β2-GPI-derived peptides described herein will attenuate tumor growth and vascularization with significantly improved pharmacokinetics.

The invention also provides methods of treating a condition associated with IR injury or inhibiting tissue damage caused by ischemia and/or reperfusion. In general, the methods comprise administering to a subject (e.g., a mammal) a therapeutically effective amount of a therapeutic peptide described herein. As used herein, a "therapeutically effective" amount refers to the amount of the peptide or other agent that will elicit the biological or medical response of a tissue, system, animal or human that is being sought by a researcher or clinician, and in particular elicit some desired therapeutic effect. For example, in one or more embodiments, a therapeutically effective amount of peptide is an amount that reduces tissue damage associated with IR. One of skill in the art recognizes that an amount may be considered therapeutically effective even if the condition is not totally eradicated but improved partially. Particularly preferred peptide dosages are discussed in more detail herein. Advantageously, the peptides compete with serum protein β2-GPI and inhibit its binding to tissue, such as epithelial tissue, thereby preventing or inhibiting tissue damage. For example, the peptides bind hypoxic cells and attenuate inflammation during reperfusion.

The peptides are suitable for prophylactic or therapeutic use. A "prophylactic" treatment is a treatment administered to a subject who does not yet exhibit signs of the condition or exhibits only early signs of the condition, for the purpose of decreasing the risk of developing pathology. Thus, the peptides can be used to reduce the likelihood of developing the condition or to minimize the severity of the condition, if developed. A "therapeutic" treatment is a treatment administered to a subject who exhibits signs or symptoms of the condition for the purpose of diminishing or eliminating those signs or symptoms or their severity.

The peptides are effective for preventing or inhibiting tissue damage when administered before or even after an ischemic event (i.e., before ischemia occurs or after ischemia and during reperfusion). In one or more embodiments, the peptides are preferably administered at any time up to about 15 minutes before ischemia begins, more preferably less than about 10 minutes before ischemia begins, and even more preferably from about 5 to about 10 minutes before ischemia begins. In additional embodiments, the peptides can be administered at any time point during reperfusion (i.e., up until the tissues are 100% reperfused). Preferably, the peptides are administered less than about 60 minutes after the ischemic event (i.e., during reperfusion), more preferably less than about 30 minutes, and even more preferably from about 5 to about 15 minutes after the ischemic event. In some embodiments, the peptides can be administered before and after the ischemic event. In one or more embodiments, the peptides can be administered via a single discrete dose (e.g., single injection), or the peptides can be administered in a continuous manner, such as via an i.v. drip.

The methods of the invention are particularly suitable for preventing or inhibiting intestinal damage and inflammation, as well as damage in tissues such as the lungs and liver. The terms "preventing" or "inhibiting," as used herein with respect to conditions associated with IR, mean that the peptide effectively attenuates, mitigates, or otherwise lessens damage that occurs during reperfusion, such that the overall degree or severity of injury is less (and preferably significantly less) than that which would have occurred if the peptide had not been administered. Intestinal IR-induced injury is considered herein to be "significantly less" if the average injury score of over 100 villi is decreased by at least 1 point, when scored according to the six-tiered scale described in Example 1, or when the p value of either an unpaired T test or one-way ANOVA of the average injury score of over 100 villi is less than or equal to 0.05. Inflammation is considered to be "significantly less" when the p value of either an unpaired T test or one-way ANOVA of the average of an inflammatory component is less than or equal to 0.05. Thus, the term "prevent" as used herein, does not necessarily mean one hundred percent avoidance of damage, inflammation, or other occurrence of the condition.

The present invention is also suitable for treating cancers, and specifically preventing or inhibiting tumor growth. The terms "preventing" or "inhibiting," as used herein with respect to tumor growth, mean that the peptide effectively attenuates, mitigates, or otherwise lessens the rate of tumor growth, such that the overall size of the tumor is less (and preferably significantly less) than if the peptide had not been administered. Preferably, growth of the peptide is lessened to such a degree that growth is effectively stopped. In some embodiments, the growth of the tumor may be reversed. A tumor is considered herein to be "significantly" smaller in size when the p value of either an unpaired T test or one-way ANOVA of the average tumor size is decreased such that p is less than or equal to 0.05. Advantageously, the peptides can be administered as an effective chemotherapeutic agent before and/or after tumor development. Cancers that can be treated include, without limitation, melanomas, breast cancers, colon cancers, and the like.

For any of the treatment methods discussed above, the peptides can be administered to the subject via intravenous (i.v.), intraperitoneal (i.p.), subcutaneous (sub Q.), retro-orbital, and/or direct injection. The peptides are preferably administered at a level of from about 0.3 to about 20 mg/kg weight of the subject, more preferably from about 1 to about 10 mg/kg weight of the subject, and even more preferably from about 3 to about 7.5 mg/kg weight of the subject.

Preferably, the peptides are administered as part of a (pharmaceutical or veterinary) composition. Thus, in one or more embodiments, the invention is also concerned with pharmaceutical or veterinary compositions comprising (consisting essentially or even consisting of) the peptide, for example, dispersed or dissolved in a pharmaceutically-acceptable carrier or excipient. The composition can be provided in any suitable form depending upon the method of administration including liquid, vial, capsule, tablet, gel (including hydrogel), suspension, and/or aerosol. As used herein, the phrase "pharmaceutically-acceptable" means not biologically or otherwise undesirable, in that it can be administered to a subject without excessive toxicity, irritation, or allergic response, and does not cause any undesirable biological effects or interact in a deleterious manner with any of the other components of the composition in which it is contained. A pharmaceutically-acceptable carrier or excipient would naturally be selected to minimize any degradation of the active ingredient (i.e., peptides or other therapeutics) and to minimize any adverse side effects in the subject, as would be well known to one of skill in the art.

Pharmaceutically-acceptable ingredients include those acceptable for veterinary use as well as human pharmaceutical use. Exemplary carriers and excipients include aqueous solutions such as normal (n.) saline (~0.9% NaCl), sterile water, phosphate buffered saline (PBS), ringers lactate and/or dextrose, as well as other solvents including dimethyl sulfoxide (DMSO), ethanol, sugars, milk proteins, gelatin, animal or vegetable oils, and/or glycerol. If necessary, the peptide can first be dissolved in a solvent before being further diluted in an aqueous solution. The concentration of the peptides in the composition will vary, but will generally range between about 4 μM to about 80 μM, preferably from about 4 μM to about 40 μM, and more preferably from about 10 μM to about 40 μM. The composition can further comprise pharmaceutically-acceptable buffers and/or salts. In one or more embodiments, the pharmaceutical composition can further comprise additional prophylactic or therapeutic agents (e.g., medicines, small molecule drugs, biologics, monoclonal antibodies, vitamins, and/or minerals) dispersed or dissolved in the carrier along with the peptide. Alternatively, the peptide can be co-administered with a separate composition containing one or more of the above prophylactic or therapeutic agents.

For example, peptides according to the invention can be co-administered with tissue plasminogen activator (TPA) or other clot-dissolving agents so that the peptides can prevent or inhibit injury from the reperfusion that occurs once the clot is unblocked. The peptides could also be co-administered with an anti-coagulant, such as heparin or coumadin, or an anti-platelet such as aspirin. Similarly, the peptides can be used in combination (as part of the same composition or in separate compositions co-administered) with therapeutic agents for treating cancer. Unless otherwise specified, "co-administration," as used herein, is intended to embrace administration of each ingredient in a sequential manner (e.g., as part of separate compositions) as well as administration of ingredients in a substantially simultaneous manner, such as in a single composition or in doses given separately (e.g., as part of discrete compositions), but nonetheless administered substantially simultaneously.

The peptides disclosed herein and their derivatives may be used in any disease or condition, which results in reperfusion injury. This would include heart attack, stroke, bypass surgery, hemorrhage, tourniquet use during trauma, organ transplantation, and mesenteric ischemia. For example, during intestinal surgery, peptide inhibitors could be administered prior to clamping of vessels. Likewise, during heart bypass surgery or after a heart attack, the peptides could be administered to prevent or inhibit damage from reperfusion after removal of the blockage. Similarly, during carotid endarterectomy, surgeons may deliberately reperfuse the tissue by re-vascularization, which can be done in conjunction with administration of the peptides to minimize tissue damage. Likewise, when a tourniquet is applied by a first responder, the i.v. bag could include the peptide inhibitors to prevent or inhibit reperfusion injury when the tourniquet is released. Similarly, during organ transplantation, the peptides can be administered prior to implanting a new organ and attaching the blood vessels, or peptides could be perfused into the donated organ during transport. The peptides would also be useful in treating deep vein thrombosis by preventing or inhibiting damage that would result from reperfusion when a clot is cleared. Likewise, during hemorrhage, the body shunts blood to the vital organs and away from the intestine resulting in an ischemic gut. Thus, the peptides can be administered when a blood transfusion and/or other fluids are given to the subject for hemorrhage, to avoid injury when the gut is reperfused. Heat stroke is another condition that causes the body to shunt more than 25% of the total blood volume to the skin. The intestine is deprived of blood and becomes ischemic similar to hemorrhage. Again, the peptide inhibitors can be administered to the subject (e.g., separately, or as part of fluids given to the subject), to prevent or inhibit damage once normal blood flow returns. As a therapeutic, the peptides are also useful for preventing multiple organ failure in response to sepsis.

The peptide inhibitors can also be used in treating other conditions not directly related to IR. For example, in an APLS miscarriage, anti-phospholipid antibodies cross the placenta and bind to the fetus resulting in miscarriage, often during the second trimester of pregnancy. The peptides of the invention can be administered to a pregnant subject or fetus to compete with the tissue and prevent antibody binding. Similarly, systemic lupus erythematosus is a condition which also involves anti-β2-GPI antibodies, which appear to induce tissue damage, and the inventive peptides may be a useful therapeutic for these patients as well. Finally, as discussed above and herein, the peptides are also useful for treating cancers and inhibiting or preventing the growth of cancerous tissues.

Additional advantages of the invention will be apparent to those in the art upon review of the disclosure herein and the working examples below.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

EXAMPLES

Figure 1C:
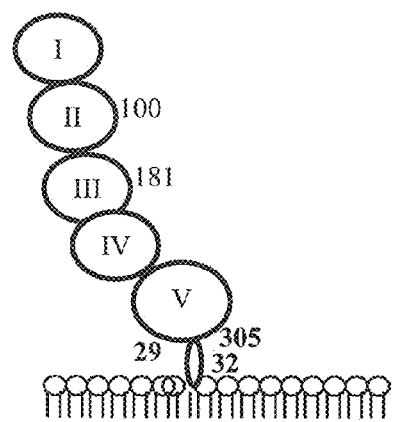
FIG. 1(C) is a schematic drawing of β2-GPI binding to a lipid membrane.

The following examples set forth methods in accordance with the invention. It is to be understood, however, that these examples are provided by way of illustration and nothing therein should be taken as a limitation upon the overall scope of the invention.

firmed by the manufacturer. We hypothesized that if inhibition of antibody binding to β2-GPI on the tissue attenuated injury, then peptides which block the lipid-binding domain of β2-GPI may inhibit β2-GPI binding thereby reducing IR-induced intestinal damage and inflammation as well. Peptides were designed to match sequences from multiple domains of mouse β2-GPI, including domains II, III and lipid-binding domain V, as indicated in the Table below and FIG. 1(A), which shows a ribbon diagram of human β2-GPI with peptide locations identified by color, peptide 100 (gold), peptide 181 (green), peptide 296 (red), peptide 322 (dark blue) and overlapping peptide 305 (light blue). Inset is magnification of Domain V. Within domain V, three overlapping peptides were created, 296, 305 and 322 based upon the NCBI sequence, AAB30789, to cover the lysine rich domain (296) and the tail which is inserted into the lipid membrane (322) with peptide 305 spanning the intervening region, as shown in FIG. 1(B). A derivative of peptide 296 was also generated using traditional solid-phase synthesis with 9-fluorenylmethoxycarbonyl chemistry, as described in detail previously (Iwamoto et al., Int. J. Peptide Protein Res. (1996)), but included a Cys to Ser substitution from the native sequence. Additional peptides 100 and 181 from Domains II and III were used as controls. FIG. 1(C) is a schematic of β2-GPI binding to a lipid membrane with the peptide locations indicated. The peptide sequences, along with their corresponding molecular weights ("MW"), are provided in Table 1 below.

TABLE 1

β2-GPI Peptide Sequences

| Peptide Name | Sequence | Residue numbers | MW (Da) |
|---|---|---|---|
| 100 | H-KNISFACNPGFFLNG-NH2 (SEQ ID NO. 16) | 105-118 | 1627 |
| 181 | H-GNDTVMCTEQQN-NH2 (SEQ ID NO. 17) | 182-193 | 1338 |
| 296 | H-IHFYCKNKEKKCSYTVEAHCRDGTI-OH (SEQ ID NO. 9) | 269-320 | 2974 |
| 296 Cys-Ser | H-IHFYSKNKEKKSSYTVEAHSRDGTI-OH (SEQ ID NO. 9) | 296-320 | 2925 |
| 305 | H-KKCSYTVEAHCRDGTIEIPSCFKEHS-OH (SEQ ID NO. 10) | 305-330 | 2969 |
| 322 | H-IPSCFKEHSSLAFWKTDASELTPC-NH2 (SEQ ID NO. 18) | 322-345 | 2629 |

Example 1

Role of β2-GPI in Ischemia and Reperfusion Injury

1. β2-GPI Peptides

The entire mouse β2-GPI sequence (SEQ ID NO. 14) was used to test the effect of β2-GPI on ischemia and reperfusion ("IR") injury in mice. Sequence fragments and derivatives synthesized based upon mouse β2-GPI were also tested. Various peptides from mouse β2-GPI were designed and then either synthesized in-house or special-ordered from Invitrogen (Carlsbad, Calif.) with purity (>90%) and sequence con- The peptides were all purified by reversed-phase HPLC and characterized by matrix-assisted laser desorption time-of-flight mass spectroscopy. All lyophilized peptides were stored at −20° C. until time of use.

2. In Vitro Hypoxia and Immunocytochemistry

MS-1 endothelial cells were subjected to hypoxia or normoxia to validate β2-GPI binding in vitro. Hypoxic MS-1 endothelial cells (ATCC CRL-2279) received degassed, serum-free DMEM and were placed in a hypoxia chamber containing 94% nitrogen and 5% $CO_2$. Normoxic cells received DMEM supplemented with 10% heat-inactivated sera from Rag-1$^{-/-}$ mice in 8% $CO_2$. After 4 hours at 37° C., all cells received fresh medium containing 10% heat-inactivated Rag-1$^{-/-}$ sera and were incubated in normoxic conditions for 1 hour at 37° C. Additional peptide-inhibition studies were performed by addition of peptides (40 μM final concentration) during the hypoxic period. Cells were methanol fixed and stained with the anti-β2-GPI mAb (Millipore; Billerica, Mass.) followed by an anti-mouse IgG antibody to determine β2-GPI binding. Anti-β2-GPI binding was determined by allowing anti-β2-GPI mAb (Millipore) to bind during the 1 hour normoxic period. The cells were then stained with anti-mouse IgG antibodies (Jackson ImmunoResearch; West Grove, Pa.) as previously described (Fleming, S. D. et al., *J. Immunol.* 173:7055-7061 (2004)). Slides were mounted with DAPI (Blue) to identify the nuclei. The fluorescence was determined in a blind manner using a Nikon 80i fluorescent microscope with a 40× Plan Fluor objective and images acquired using a CoolSnap Cf camera (Photometrics; Tucson, Ariz.) and MetaVue Imaging software (Molecular Devices; Sunnyvale, Calif.). Each photomicrograph in the Figures is representative of 3 experiments with 4-6 photomicrographs per treatment group in each experiment. Bar=40 µm.

3. Mice

C57Bl/6 and Rag-1$^{-/-}$ (backcrossed to C57Bl/6 for 10 generations) mice were purchased from The Jackson Laboratory (Bar Harbor, Me.) and bred and maintained under 12-hour light/dark cycles at Kansas State University, Division of Biology (Manhattan, Kans.). All mice were allowed access to food and water ad libitum and maintained under specific pathogen-free conditions. Research was conducted in compliance with the Animal Welfare Act and other federal statutes and regulations relating to animals and experiments involving animals and was approved by the Institutional Animal Care and Use Committee.

4. Ischemia/Reperfusion Procedure

C57Bl/6 and Rag-1$^{-/-}$ mice were subjected to ischemia followed by reperfusion similar to previously described studies (Moses, T. et al., *J. Leukoc. Biol.* 86:971-980 (2009)). Briefly, ketamine (16 mg/kg) and xylazine (80 mg/kg) were used to anesthetize the mice. Buprenorphine (0.06 mg/kg) was then administered for pain. A midline laparotomy was performed to expose the abdominal cavity of the mice, which were then allowed to equilibrate for 30 min. Body temperature was maintained at 37° C. using a water-circulating heat pad. Placing a warm, saline moistened piece of gauze over the abdominal cavity prevented peritoneal desiccation. Next, a small vascular clamp (Roboz Surgical Instruments; Gaithersburg, Md.) was applied to the isolated superior mesenteric artery to cut off blood flow to the intestines. Ischemia was noted by the intestine changing from a pink color to a gray color. After 30 min of ischemia, the clamp was removed and the intestines were allowed to reperfuse for 5, 10, 15, or 120 min. Sham animals sustained the same surgical intervention without superior mesenteric artery occlusion. Mice treated with the various β2-GPI peptides underwent the same procedure with i.v. administration of the peptides (40 µM) 5 min prior to artery occlusion. Peptides 296, 305, and 296Cys to Ser were dissolved in N. Saline (0.9% NaCl) and injected i.v. in 100-µL volumes. Peptides 100 and 181 were dissolved in DMSO prior to diluting 1/100 in N. Saline. Additional mice received peptides prior to Sham treatment.

In some experiments, 200 µL of C57Bl/6 sera with or without the reduction of anti-β2-GPI Ab was administered i.v. to Rag-1$^{-/-}$ mice 20 min prior to clamp application. After euthanasia, the mid-jejunum, 10-20 cm distal to the gastroduodenal junction was removed for analysis. Survival was not significantly different between treatment groups.

5. Histology and Injury Scoring

Immediately after euthanasia, a 2-cm mid jejunum tissue section was immediately fixed in 10% buffered formalin, embedded in paraffin, and 8 µm sections were cut transversely and hematoxylin and eosin (H&E) stained. Mucosal injury was graded on a six-tiered scale, as described previously (Fleming, S. D. et al., *J. Immunol.* 169:2126-2133 (2002)). Briefly, the average damage score of the intestinal section (75-150 villi) was determined after grading each villus. Normal villi were assigned a score of zero; villi with tip distortion were assigned a score of 1; a score of 2 was assigned when Guggenheims' spaces were present; villi with patchy disruption of the epithelial cells were assigned a score of 3; a score of 4 was assigned to villi with exposed, but intact, lamina propria with epithelial sloughing; a score of 5 was assigned when the lamina propria was exuding; and villi that displayed hemorrhage or were denuded were assigned a score of 6. Photomicrographs were obtained from H&E stained slides using a 20×, 0.5 Plan Fluor objective on a Nikon 80i microscope and images acquired at room temperature using a Nikon DS-5M camera with DS-L2 software.

6. Ex Vivo Eicosanoid and Cytokine Generation

Ex vivo generation of eicosanoids by mid-jejunal tissue was determined. Immediately after collection, a 2-cm intestinal section from each mouse was minced, washed, resuspended in 37° C. oxygenated Tyrode's buffer (Sigma-Aldrich; St. Louis, Mo.), incubated at 37° C. for 20 minutes, and the supernatant collected. $PGE_2$ and $LTB_4$ concentrations were determined using enzyme immunoassay kits (Cayman Chemical; Ann Arbor, Mich.). IL-6 and IL-12 concentrations were determined using a Milliplex MAP immunoassay kit (Millipore) and read on a Milliplex Analyzer (Millipore). All eicosanoid and cytokine concentrations were standardized to the total tissue protein content.

7. C3 Deposition and Immunohistochemistry

After euthanasia, an additional 2-cm intestinal section from each mouse was immediately snap frozen in O.C.T. freezing medium and 8 µm sections were placed on slides for immunohistochemistry. The C3 deposition and F4/80 expression on the tissue sections were detected by staining with a purified rat-anti-mouse C3 (Hycult Biotechnologies; Plymouth Meeting, Pa.) or F4/80 (eBioscience; San Diego, Calif.) antibody followed by a Texas-red conjugated donkey-anti-rat IgG secondary antibody (Jackson Immunoresearch). CD31 (PECAM-1) and CD106 (VCAM-1) were detected by FITC conjugated rat anti-mouse CD31 or CD106 (Biolegend; San Diego, Calif.) antibodies. Each experiment contained serial sections stained with the appropriate isotype control antibodies. All slides were mounted with ProLong Gold (Invitrogen). Images were obtained at room temperature using a Nikon Eclipse 80i microscope equipped with a CoolSnap CF camera (Photometrics) and analyzed using Metavue software (Molecular Devices). The fluorescence was semi-quantitated using Image J software (NIH) using the fluorescent area fraction after setting threshold for each experiment. The average of the isotype control was subtracted from each photo. The average of 6-10 photos/tissue from 3-5 animals per treatment group is shown in the Figures.

8. Immunoprecipitation of β2-GPI Complexes From Tissue

Mid-jejunum (25-30 mm) was longitudinally opened, adhered to a 6-well plate and incubated at 4° C. for 2 hours in freshly oxygenated Tyrode's buffer containing 15 µg/mL FC1 mAb (mouseIgG1, anti-β2-GPI) (Monestier, M. et al., *J. Immunol.* 156:2631-2641 (1996)). The crosslinker, DTSSP (Pierce), was added to the Ab solution at a final concentration of 1.5 mM and incubated at 4° C. for an additional 2 hours. The reaction was stopped with Tris, pH 7.5 and the washed mucosa was then lysed in 1 mL of MES/Brij58 (145 mM NaCl, 0.2 mM EDTA, 0.5% w/v Brij58 (Sigma-Aldrich), 25 mM MES (Sigma-Aldrich), pH 6.5). The lysate was then incubated for 30 min on ice, with periodic vortexing, followed by clarifying via centrifuge at 5,000×g for 10 min at 4° C. Antibody was then immunoprecipitated overnight at 4° C. with Protein G beads (ThermoScientific; Rockford, Ill.) and the samples were boiled in non-reducing Laemmli sample buffer prior to SDS-PAGE (10%) and Western blot analysis. Human β2-GPI (Fitzgerald; North Acton, Mass.) was used as a positive control. The blots were probed with anti-β2-GPI antibody, MAB1066 (Chemicon; Billerica, Mass.), followed by goat anti-mouse IgG HRP conjugate (ThermoScientific). Protein was visualized using SuperSignal Detection Kit (ThermoScientific) according to the manufacturer's protocol.

9. Anti-β2-GPI Concentrations and Isotyping

Anti-β2-GPI concentrations were determined based on optimal conditions previously described (Cavazzana, A. et al., *Ann. N.Y. Acad. Sci.* 1109:484-492 (2007); Wong, R. C. et al., *Pathology* 40:58-63 (2008)). The specific isotypes of anti-β2-GPI antibodies were determined after binding serum in duplicate to coated and blocked wells and incubating for 1 hour. After washing, the appropriate biotinylated anti-mouse Ig isotype antibodies were added to each well for 1 hour at RT while gently shaking After incubation with avidin peroxidase (Sigma-Aldrich) the plate was developed using TMB (Kirkegaard).

10. Reduction of Anti-β2-GPI Activity From C57Bl/6 Serum

An ELISA plate was coated for 2 hours at room temperature with 2 μg of β2-GPI (Fitzgerald) in PBS. After blocking for 2 hours with 100 μL of 3% bovine serum albumin in PBS, 50 μL of heat-inactivated C57Bl/6 sera was added to half of the coated wells for 2 hours at room temperature. The sera was then transferred to the remaining coated set of wells and incubated for an additional 2 hours at room temperature. The reduced serum was removed, pooled and then administered as described above. The reduction procedure removed approximately 50% of the anti-β2-GPI antibodies as determined by ELISA.

11. Statistical Analysis

Data are presented as mean±SEM and significance ($p<0.05$) determined by one-way ANOVA with Newman-Keuls post hoc analysis (GraphPad/Instat Software).

12. Results a. In Vitro Hypoxia and Normoxia Results

Figure 2:
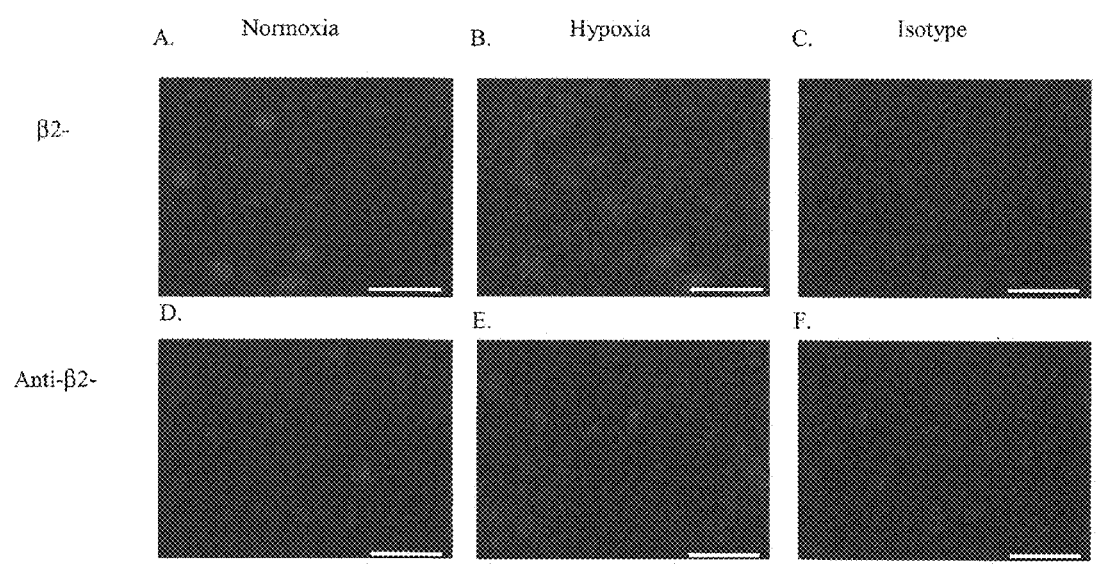
FIG. 2 shows photomicrographs of stained cells from the hypoxia and normoxia experiments in Example 1.

Initial in vitro studies tested the ability of the peptides to block β2-GPI binding to hypoxic endothelial cells. The results are shown in FIG. 2. As described above, cells were subjected to 4 hours of normoxia in media containing 10% heat-inactivated Rag-1−/− sera (A, D) or hypoxia under serum-free conditions (B-C, E-F), followed by 1 hour of normoxia in media containing 10% Rag-1−/− serum in the absence (A-C) or presence of anti-β2-GPI (D-E) or isotype control (F) antibody. The cells were fixed with methanol, probed with a primary anti-β2-GPI antibody (A-B) or isotype control antibody (C) then stained with an anti-mouse secondary or stained with a Texas-red labeled anti-mouse secondary antibody only (Red; D-F). Addition of sera from Rag-1−/− mice during the subsequent normoxia (reperfusion) stage provided the β2-GPI. After hypoxic but not normoxic treatment, cells were positive for β2-GPI (FIG. 2A-C). The addition of anti-β2-GPI mAb to the cells during reperfusion, again showed that only hypoxic but not normoxic-treated cells stained positively for anti-β2-GPI antibodies (FIG. 2D-F). Similar to the in vivo results discussed herein, in vitro studies showed that hypoxia-induced cellular changes facilitated the binding of both β2-GPI and anti-β2-GPI antibodies to the surface of ischemic cells.

Figure 3:
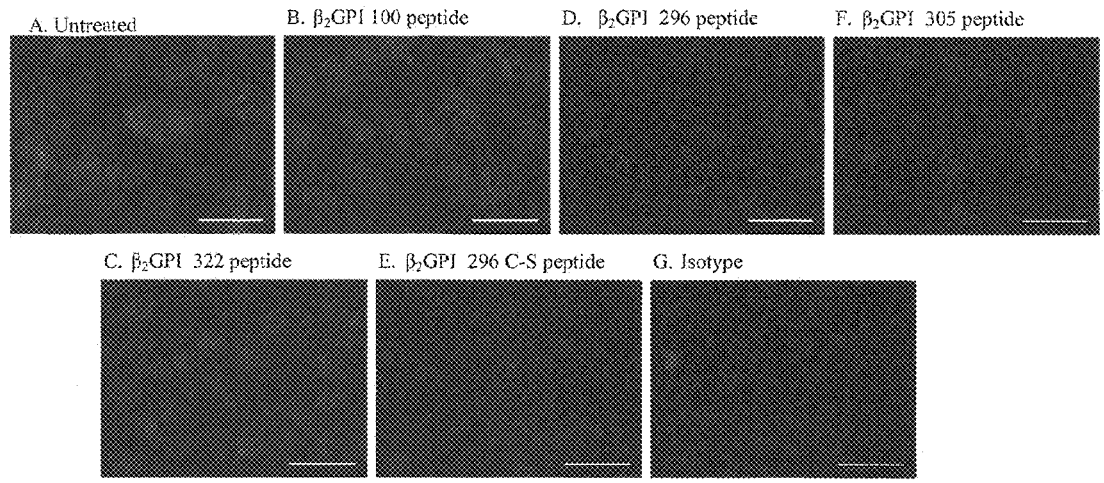
FIG. 3 shows photomicrographs of additional stained cells from the hypoxia and normoxia experiments in Example 1.

As indicated in FIG. 3, after 4 hours hypoxia, anti-β2-GPI mAb was bound to untreated MS-1 cells significantly more than isotype control mAb. β2-GPI peptides 100 or 322 did not inhibit antibody binding to the hypoxic endothelial cell line. In contrast, anti-β2-GPI mAb did not bind to hypoxic MS-1 cells, which were pre-treated with peptides 296 or 305. Together these data indicated that the overlapping peptides 296 and 305 were capable of preventing β2-GPI from binding to hypoxic endothelial cells. The 296 Cys-Ser peptide derivative was also used in the in vitro hypoxia assay. Similar to peptide 296, the Cys-Ser substituted peptide also attenuated β2-GPI binding to the hypoxic cells.

Figure 4:
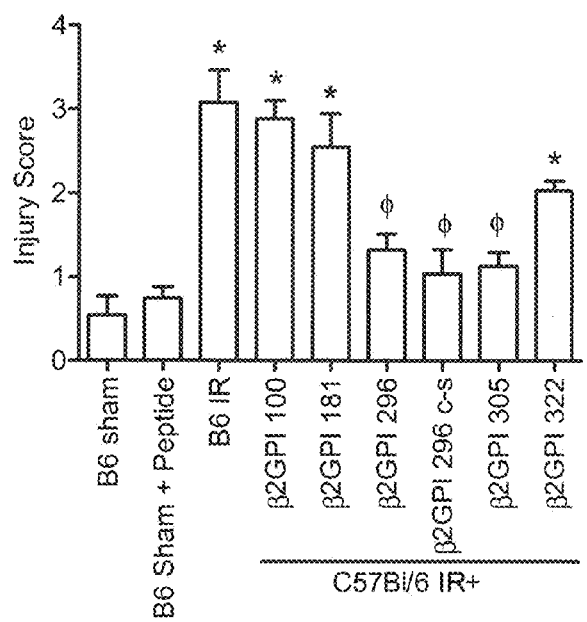
FIG. 4 is a graph showing the injury score of tissues of mice subjected to IR with or without administration of peptides in Example 1.
Figure 5:
FIG. 5 shows H&E stained intestinal tissues of mice subjected to IR with or without administration of peptides in Example 1.
Figure 5:
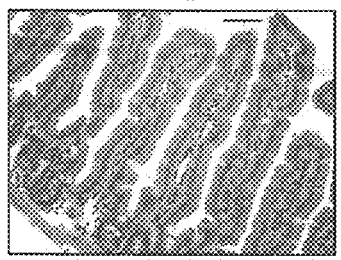
Figure 5:
Figure 5:
Figure 5:
Figure 5:
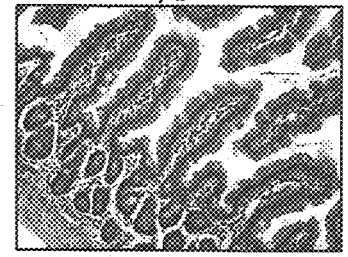
Figure 5:
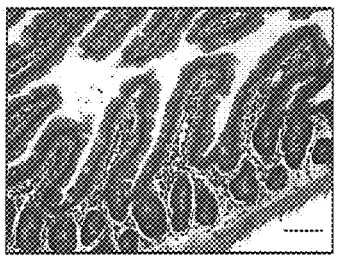
Figure 5:
Figure 5:

The in vitro hypoxia studies suggested that peptides 296 and 305 may attenuate IR-induced tissue damage. To test this hypothesis, peptides were infused into C57Bl/6 mice 5 min prior to intestinal IR and mucosal damage and inflammation evaluated.

c. Mucosal Injury and β2-GPI Binding to Ischemic or Hypoxic Tissue Occurs Early in Reperfusion Mid-jejunal sections were scored (75-150 villi per animal) from C57Bl/6 mice with or without injection of β2-GPI peptides prior to Sham or IR treatment. The results are shown in FIGS. 4 and 5. In FIG. 4, *=$p \leq 0.05$ compared to Sham+peptide, Φ=$p \leq 0.05$ compared to IR treatment animals not receiving peptides. Each bar in FIG. 4 is representative of 3-4 animals and each treatment was performed on at least 2 separate days. Representative intestinal sections H&E stained from C57Bl/6 Sham-treated mice are shown in FIG. 5. As can be seen from the data, similar to in vitro results, mice which received peptides 296, 305 or 296Cys-Ser sustained attenuated mucosal damage in response to IR. Microphotographs are representative of 3-4 animals stained in at least 3 independent experiments. Bar=50 μm. In contrast, those which received peptides 100, 181, and 322 sustained IR-induced intestinal damage similar to untreated mice. Thus, peptide inhibition of β2-GPI attenuates IR-induced intestinal damage.

Figure 6A:
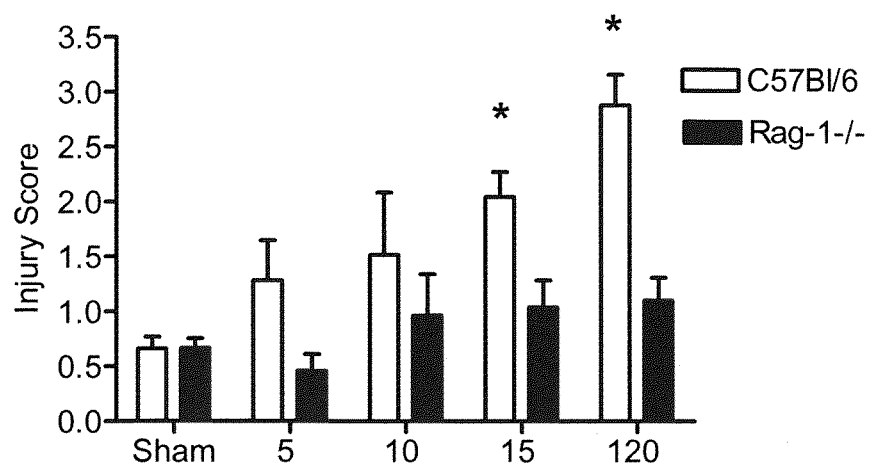
FIG. 6(A) is a graph of intestinal injury scores of mice at 5-, 10-, 15, and 120-minutes after reperfusion in Example 1.

FIG. 6(A) shows the intestinal injury scores of mid-jejunal sections collected from C57Bl/6 or Rag-1−/− mice at 5, 10 and 15 min after reperfusion or from Sham-treated mice. Compared to pooled sham-treated animals, significant mid-jejunal mucosal injury was observed after 15 min of reperfusion and increased up to 2 hours post-reperfusion in C57Bl/6 mice. In contrast, Rag-1−/− mice did not sustain intestinal damage at any time point analyzed. When analyzed for β2-GPI, sera from both C57Bl/6 and Rag-1−/− mice contained similar concentrations of β2-GPI (data not shown). As previously shown, anti-β2-GPI binds ischemic-damaged tissue within 2 hours following reperfusion (Fleming, S. D. et al., *J. Immunol.* 173:7055-7061 (2004)).

Figure 6B:
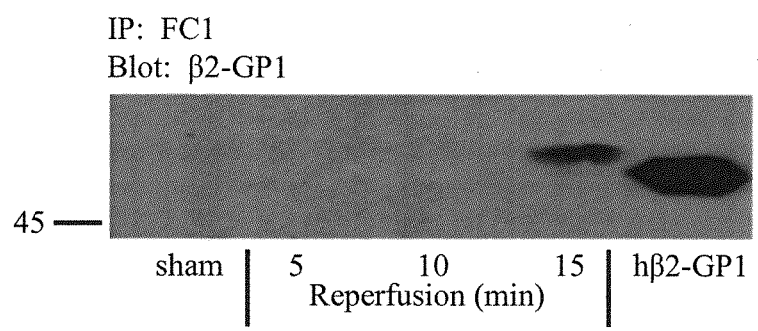
FIG. 6(B) is a Western Blot of the tissue harvested at 5-, 10-, and 15-minutes after reperfusion in Example 1.

To examine the early kinetics, tissue harvested after 5, 10, or 15 min of reperfusion was probed with the anti-β2-GPI mAb, FC1. The antibody/antigen complexes were cross-linked to the surface of the villi prior to immunoprecipitation and Western blotting. The results are shown in FIG. 6(B). Human β2-GPI (50 kDa) was run as a control for mouse β2-GPI (54 kDa). The blot shown in FIG. 6(B) is representative of 4 experiments. Immunoprecipitation indicated the presence of β2-GPI bound to the cell surface at 15 min post-reperfusion but not at the earlier time points. The apparent molecular weight difference between human and mouse is likely due to differential glycosylation and different isoelectric points (Gries, A. et al., *Biochem. J.* 260:531-534 (1989)). Additionally the presence of detectable levels of tissue-bound β2-GPI correlates positively with the earliest time point when significant damage was observed, as shown in FIG. 6(A).

d. Characterization of the Anti-β2-GPI Activity in C57Bl/6 Serum

Figure 7:
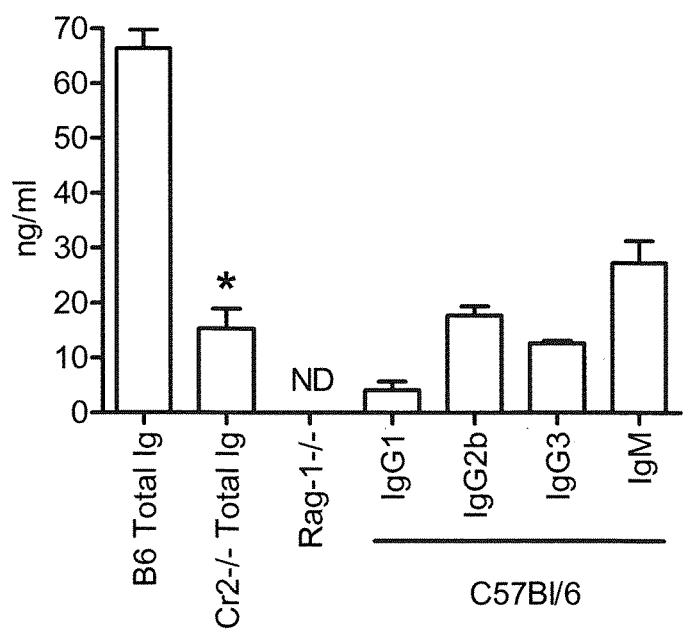
FIG. 7 is a graph of characterization of anti-β2-GPI activity in the mice in Example 1.
Figure 8:
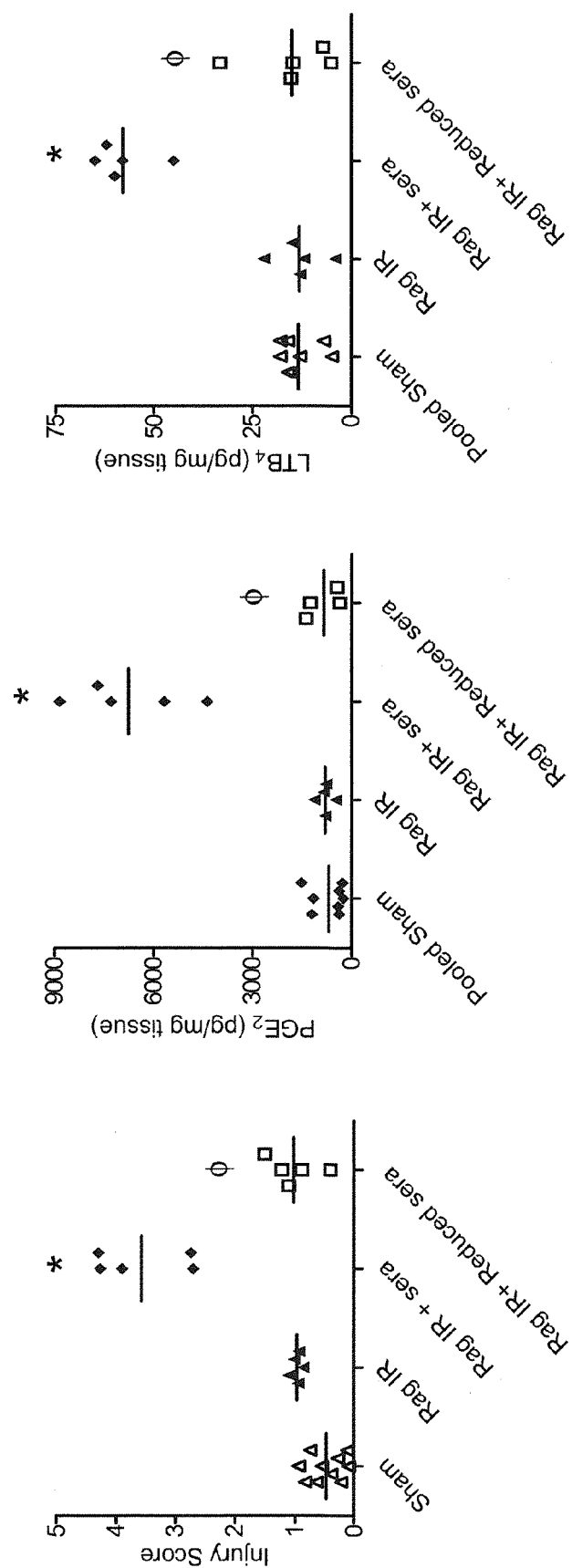
FIG. 8 shows graphs of the injury score, PGE$_2$ and LTB4 concentrations from Rag-1-/- mice subjected to IR after reconstitution with wildtype serum after to 2 rounds of adsorption to bound β2-GPI in Example 1.
Figure 9:
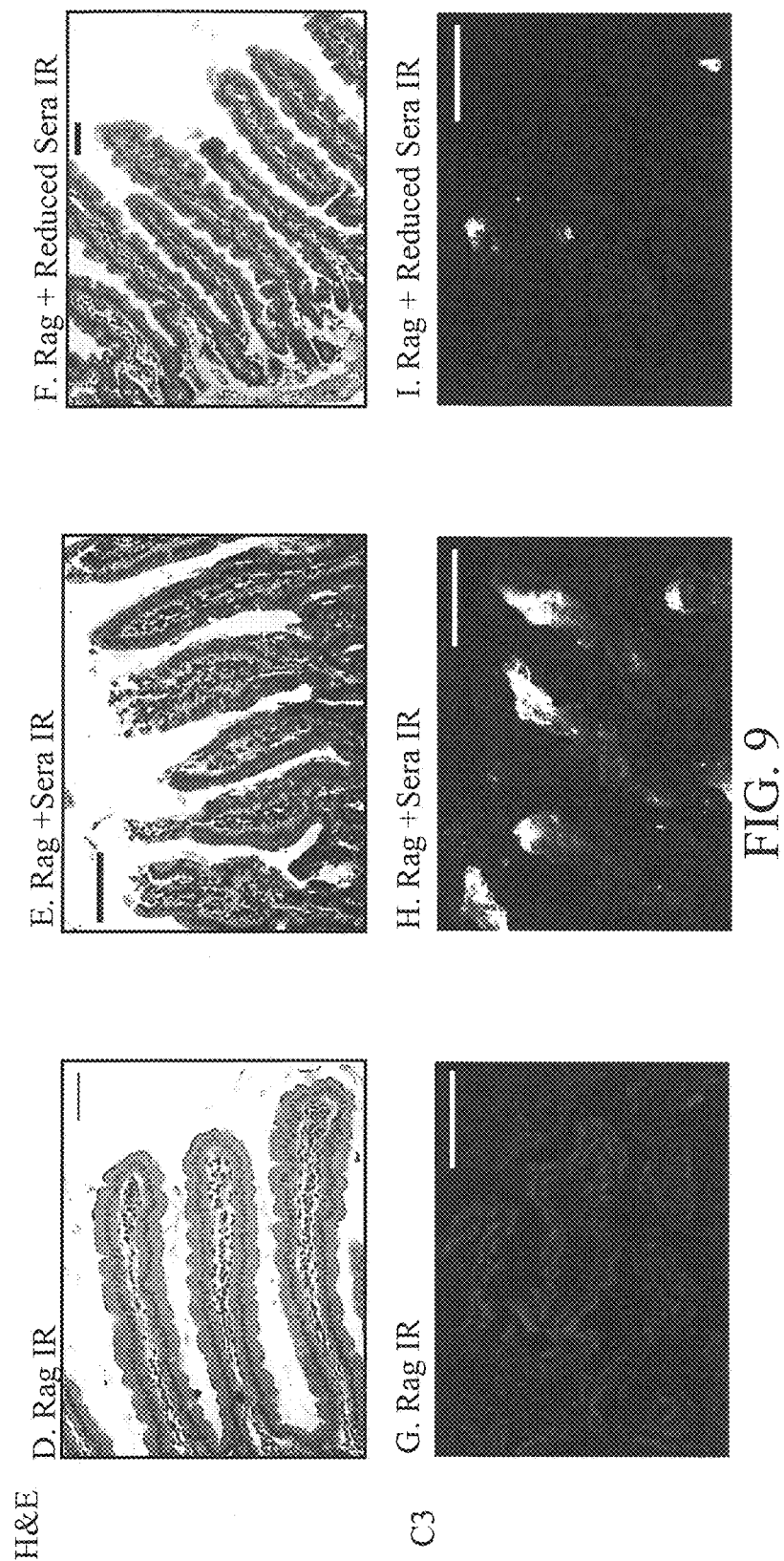
FIG. 9 shows the H&E stained tissues from the mice in FIG. 8.

To further understand the role of anti-β2-GPI antibodies, we examined the presence of these antibodies in wildtype C57Bl/6 and Rag-1$^{-/-}$ mice and compared it to Cr2$^{-/-}$ mice, as determined by ELISA. The results are shown in FIG. 7, where each bar represents the mean±SEM of 3 independent experiments, and *=p≤0.05 compared to Sham. As shown in FIG. 7, we determined that approximately 60 ng/mL anti-β2-GPI antibody (total Ig) is present in C57Bl/6 serum, but as expected, Rag-1$^{-/-}$ serum contained no detectable antibodies. Interestingly, serum from IR-resistant, Cr2$^{-/-}$ mice contains significantly less anti-β2-GPI antibody. These results indicate that naturally occurring antibodies against β2-GPI exist in wildtype mice. The anti-β2-GPI antibody concentration in wildtype sera was determined to be primarily of the IgM and IgG2b isotypes with minor amounts of IgG3 and IgG1 isotypes. The presence of IgG2b, IgG3 and IgM isotypes is consistent with complement activation. Therefore, β2-GPI represents a significant target for forming antibody/antigen complexes capable of facilitating complement-mediated tissue damage.

e. Reduction of Serum Anti-β2-GPI Activity Attenuated Intestinal Damage and Inflammation The effects of anti-β2-GPI antibody reduction on IR-mediated damage were assessed by subjecting Rag-1$^{-/-}$ mice to IR after reconstitution with wildtype serum after 2 rounds of adsorption to bound β2-GPI. The results are shown in FIG. 8 and FIG. 9. In FIG. 8, the values are represented as pg/mg of intestinal protein, where *=p≤0.05 compared to Sham, and Φ=p≤0.05 compared to animals receiving non-reduced sera. Each animal is represented by an individual point with the bar representing the average. Each treatment was performed on at least 2 separate days. FIG. 9 shows the representative intestinal sections H&E stained (A-C) or stained for C3 deposition (D-F) from IR-treated Rag-1$^{-/-}$ mice (A, D), IR-treated Rag-1$^{-/-}$ mice receiving C57Bl/6 serum (B, E), or IR-treated Rag-1$^{-/-}$ mice receiving anti-β2-GPI antibody reduced C57Bl/6 serum (C, F). Microphotographs are representative of 3-4 animals stained in at least 3 independent experiments. H&E bar=50 µm and immunohistochemistry bar=40 µm.

When Rag-1$^{-/-}$ mice were reconstituted with non-adsorbed C57Bl/6 serum, significant damage was observed after 2 hours reperfusion (FIG. 8(A)) similar to previous results for C57Bl/6 mice (FIG. 6A). However, when mice were administered anti-β2-GPI reduced serum, no damage was observed similar to that seen in Rag-1$^{-/-}$ IR control mice (FIG. 8(A) and FIG. 9(A)-(C)). Moreover, the effects of anti-β2-GPI reduction extended to dramatically decreasing the intestinal inflammatory response. The IR-induced increase in PGE$_2$ and LTB$_4$ production was abrogated with the antibody-reduced serum to concentrations similar to Rag-1$^{-/-}$ IR controls. These data suggest that inhibition of anti-β2-GPI antibodies may provide a therapeutic target for IR-induced tissue damage.

f. Domain V β2-GPI Peptides Block IR-Induced Intestinal Inflammation

Figure 10:
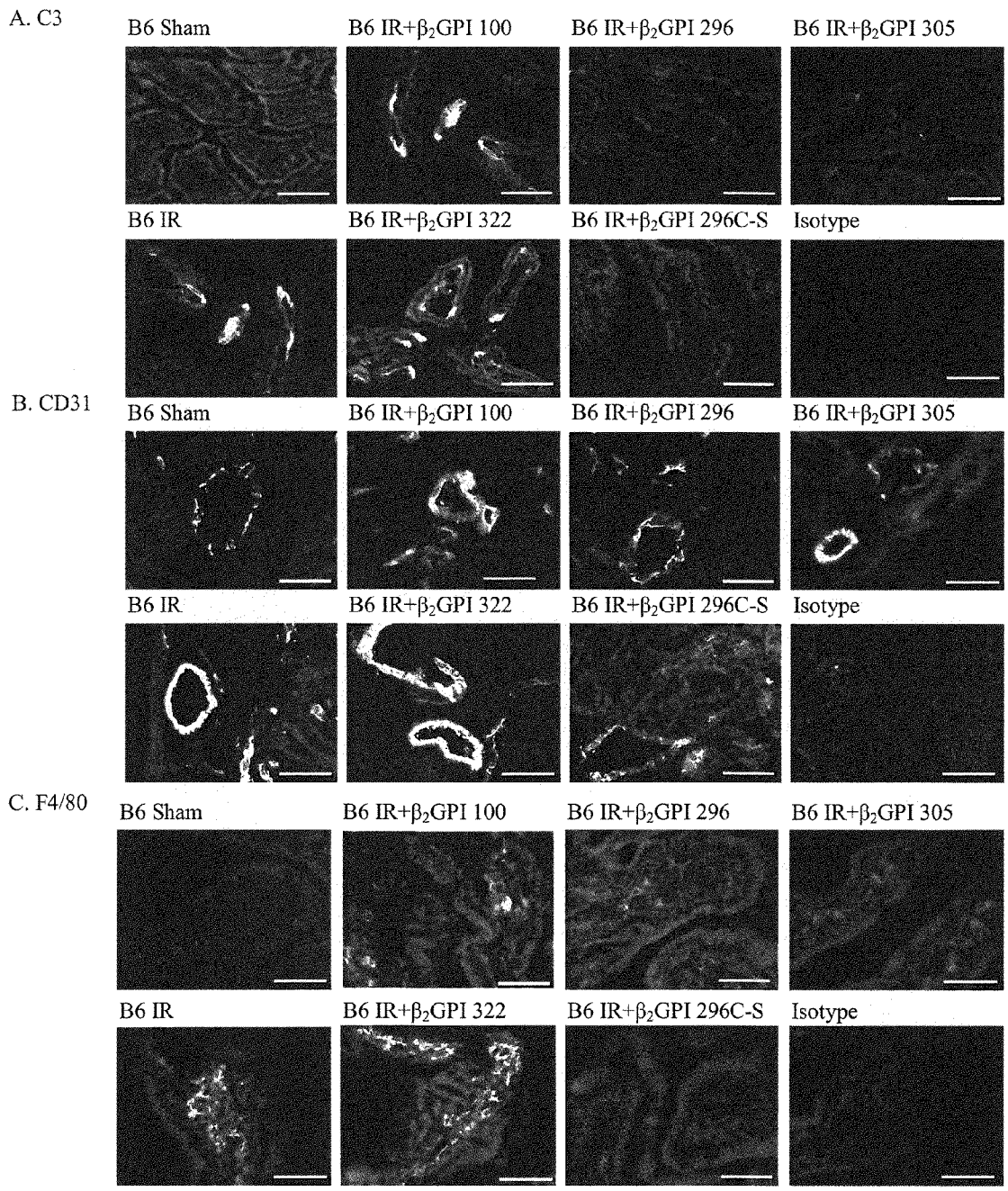
FIG. 10 shows microphotographs of intestinal tissues stained for C3, CD31, or F4/80 from mice in Example 1 subjected to IR or Sham in the presence of absence of the therapeutic peptides.
Figure 11:
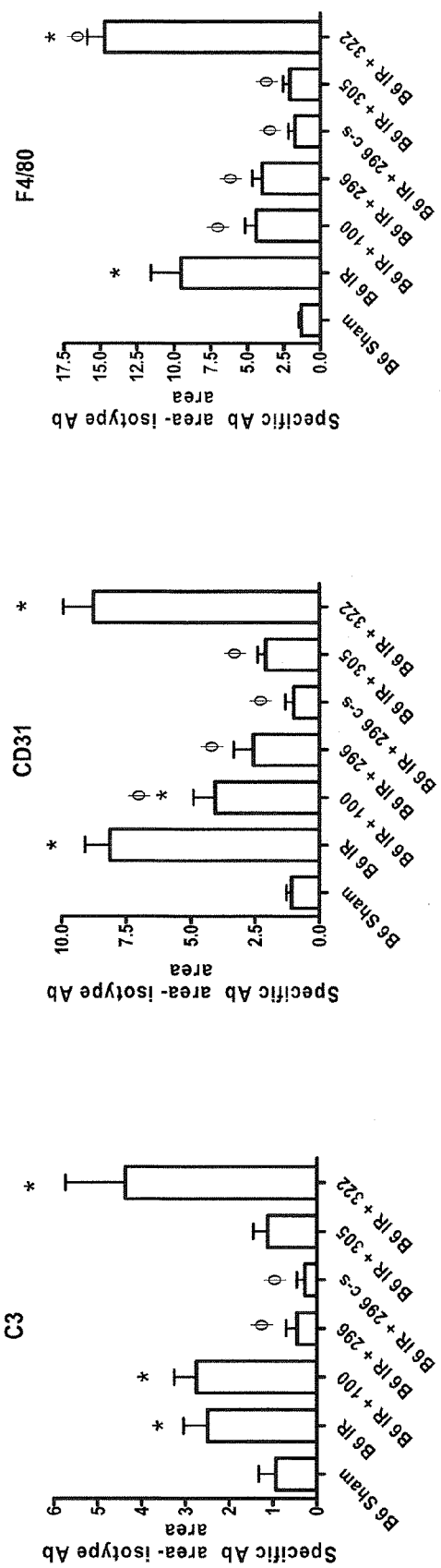
FIG. 11 shows graphs of the fluorescent fractions of the specific antibodies from the mice in FIG. 10 after subtraction of isotype control antibodies.

To examine the multiple pathways of inflammation involved in IR-induced damage, intestinal tissues from the peptide treated mice were examined for complement deposition, adhesion molecule expression and the macrophage marker, F4/80. The results are shown in FIG. 10 and FIG. 11. FIG. 10 shows the representative intestinal sections stained for C3 (A), CD31 (B), or F4/80 (C) from Sham-treated C57Bl/6 mice, IR-treated C57Bl/6 in the absence or presence of β2-GPI peptides as indicated. The microphotographs are representative of 3-4 animals stained in at least 3 independent experiments. Bar=40 µm. Fluorescence was semi-quantitated using Image J software (NIH) and is reported in FIG. 11 as fluorescent fraction of specific antibodies after subtraction of the fluorescent fraction of isotype control antibodies. *=p≤0.05 compared to Sham+peptide and Φ=p≤0.05 compared to IR treatment animals not receiving peptides. Each bar is representative of 3-5 animals with 6-10 photos analyzed per animal.

As expected, IR induced C3 deposition on the intestines of C57Bl/6 mice in response to IR but not Sham treatment (FIG. 10(A)). Similar to injury results, peptides 100 and 322 did not significantly inhibit C3 deposition (FIG. 10(A), FIG. 11). In addition, infusion of peptides 296 and 296Cys-Ser prior to IR significantly decreased C3 deposition (FIG. 10(A), FIG. 11). Interestingly, peptide 305 was not significantly different from either Sham or IR treatment (FIG. 11). Similarly, the expression of adhesion molecules, CD31 and VCAM, was inhibited after treatment with peptides 296, 305 and 296Cys-Ser but not after treatment with peptide 322 (FIG. 10(B), FIG. 11), data not shown). However, peptide 100 was significantly different from both Sham and IR treated mice. Expression of the mature macrophage marker increased in response to IR with or without peptide 322 (FIG. 10(A), FIG. 11). Treatment with peptides 100, 296, 305 and 296Cys-Ser reduced macrophage to Sham levels after treatment with peptide 296Cys-Ser (FIG. 10(C), FIG. 11).

Figure 12:
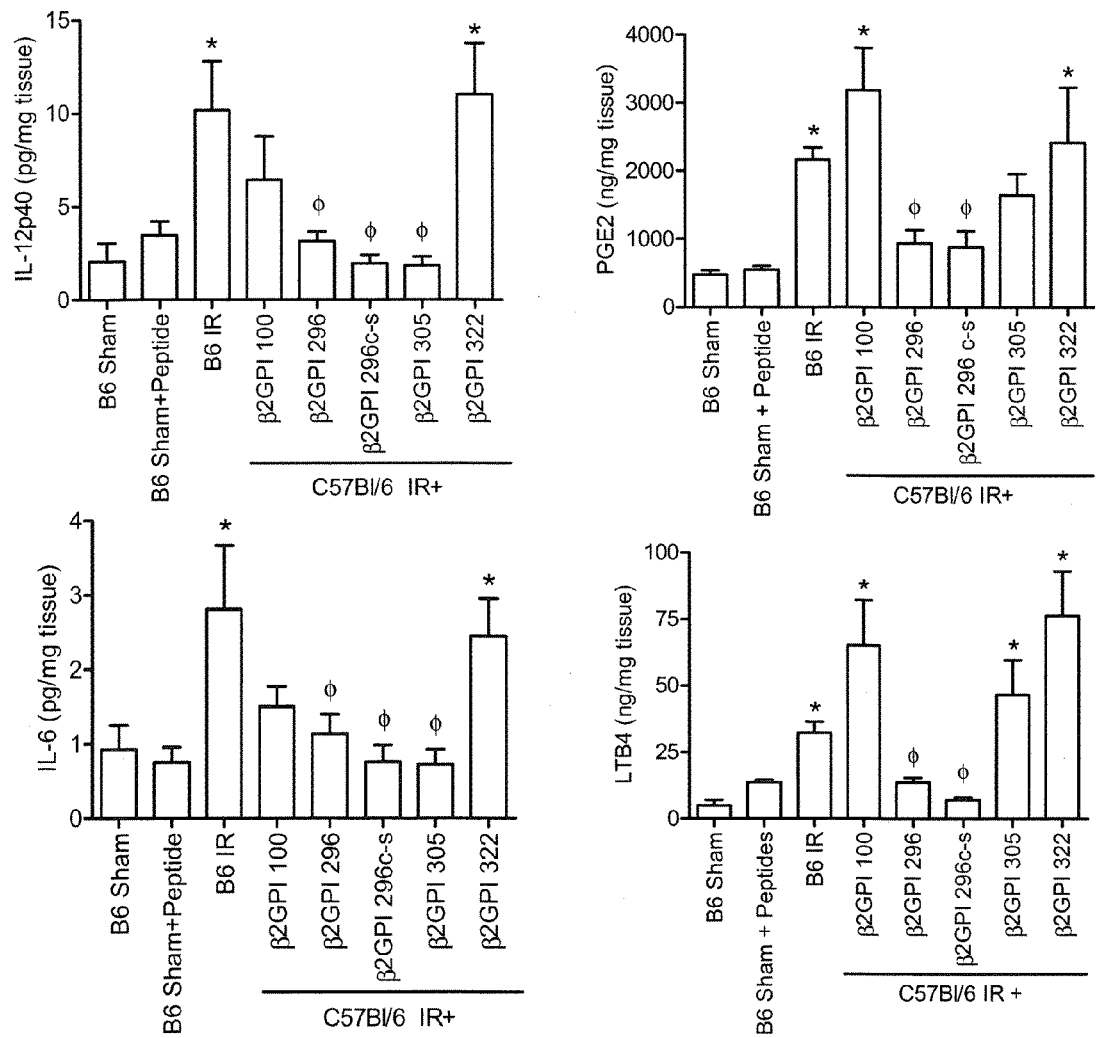
FIG. 12 shows graphs of the ability of the peptides to attenuate production of various inflammatory molecules from Example 1.

The pro-inflammatory cytokines, IL-12 and IL-6, and eicosanoids, LTB$_4$ and PGE$_2$, increase rapidly in response IR (Arumugam, T. V. et al., *Shock* 32:4-16 (2009)). Therefore, we examined the ability of peptides 296, 305 and 296Cys-Ser to attenuate production of these inflammatory molecules. The results are shown in FIG. 12, where the values are presented as pg/mg of intestinal protein, *=p≤0.05 compared to Sham, and Φ=p≤0.05 compared to animals not receiving peptide. Each bar is representative of 3-4 animals and each treatment was performed on at least 2 separate days. Similar to previous results, IR induced IL-12 and IL-6 production which was attenuated by protective peptides 296, 305 and 296Cys-Ser (FIGS. 12(A), (B)). Interestingly, peptide 100 also attenuated IL-6 production (FIG. 12(B)). However, peptide 322 did not inhibit IR-induced cytokine production (FIGS. 12(A), (B)). Thus, β2-GPI binding occurs prior to IR-induced, pro-inflammatory cytokine production.

Previous studies demonstrated that IR also induces eicosanoid production within 2 hours post-ischemia (Fleming, S. D. et al., *J. Immunol.* 169:2126-2133 (2002)). To determine if β2-GPI initiation of intestinal damage contributes to eicosanoid production, intestinal LTB$_4$ and PGE$_2$ production within the intestine was examined in mice subjected to Sham or IR in the presence or absence of the various β2-GPI peptides. Peptides 296 and 296Cys-Ser attenuated IR-induced production of both eicosanoids, while mice treated with peptides 100 and 322 sustained inflammation similar to untreated mice (FIG. 12(C)-(D)). Despite the ability to attenuate IR-induced intestinal damage, peptide 305 did not attenuate intestinal eicosanoid production (FIG. 12(C)-(D)). These data suggest that distinct residues may be critical for the inflammatory response and intestinal damage or that a critical threshold must be reached for complete injury. Together, these data indicate that β2-GPI has a role in IR-induced tissue damage and initiation of inflammation and administration of β2-GPI peptides prior to IR attenuates injury and as such may provide clinically relevant therapeutics for a condition with a high mortality rate.

13. Discussion

Both peptide inhibition of β2-GPI activity in wildtype mice and infusion of wildtype serum containing reduced levels of anti-β2-GPI antibodies into Rag-1$^{-/-}$ mice prevented IR-induced intestinal damage and inflammation. The results are summarized in Table 2 below. Thus, our results demonstrate that natural antibodies targeting β2-GPI play a critical role in initiating antibody/antigen complexes required for subsequent complement activation in response to IR. In addition, these data suggest that binding of β2-GPI to ischemic cells is critical for IR-induced damage and inflammation.

TABLE 2

Summary of IR-induced injury and inflammation in C57Bl/6 mice with or without peptide treatment

| | B6 IR$^A$ | B6 + β$_2$- 100 | B6 + β$_2$- 296 | B6 + β$_2$- 296c-s | B6 + β$_2$-305 | B6 + β$_2$-322 |
|---|---|---|---|---|---|---|
| Injury$^B$ | + | + | − | − | − | + |
| C3 Deposition | + | + | − | − | − | + |
| CD31 Deposition | + | + | − | − | + | + |
| F4/80 Deposition | + | + | − | − | − | + |
| IL-12p40 Induction | + | +/− | − | − | − | + |
| IL-6 Induction | + | +/− | − | − | − | + |
| PGE$_2$ Production | + | + | − | − | +/− | + |
| LTB$_4$ Production | + | + | − | − | + | + |

+ indicates significant difference from Sham treated mice;
− indicates not significantly different from C57B1/6 sham treated mice;
+/− indicates no significant difference from either C57B1/6 mice subjected to either Sham or IR.
$^A$C57B1/6 mice subjected to IR with or without peptide treatment.
$^B$Measure of injury or inflammation.

Reperfusion is accompanied by the production of inflammatory mediators and immune cell infiltration. IR-induced lipid changes result in increased arachidonic acid and subsequent production of the inflammatory mediators, LTB4 and PGE2. Interestingly, anti-β2-GPI antibody binding of β2-GPI induced cellular infiltration and eicosanoid generation. Importantly, all these inflammatory mediators and the IR-induced pro-inflammatory cytokines were blocked by peptides 296 and 296Cys-Ser, while peptide 305 inhibited IL-12 and IL-6 production but not eicosanoid production. Activation of complement also initiates immune cell infiltration. Treatment with peptides 296, 305, and 296Cys-Ser attenuated complement activation. The results demonstrate that peptides 296 and 296Cys-Ser inhibit IR-induced IL-12 and IL-6 as well as upregulation of adhesion molecules and subsequent increases in cellular infiltration. Thus, the lack of TLR expression may prevent intestinal damage by interfering with antibody recognition of β2-GPI.

Previous studies indicated that IR-induced damage is due to natural antibodies with reactivity to non-muscle myosin, glycogen phosphorylase or annexin IV. (Kulik, L. et al., *J. Immunol.* 182(9):5363-5373 (2009); Zhang, M. et al. *J. Exper. Med.* 203:141-152 (2006); Chan, R. K. et al., *Surgery* 139(2):236-243 (2006)). However, attenuated damage following peptide inhibition of β2-GPI binding suggests that these additional target antigens may be exposed after β2-GPI binding. It is possible that β2-GPI binding induces a signal which leads to either apoptosis with annexin IV expression or necrosis and non-muscle myosin exposure. As specific β2-GPI peptides reduced IR-induced tissue damage to Sham levels, β2-GPI appears to be a critical therapeutic target for mesenteric IR. In addition, reperfusion-induced tissue damage in response to myocardial infarction, stroke, and transplantation appears to use similar mechanisms (Arumugam, T. V. et al., *Shock* 32:4-16 (2009); Arumugam, T. V. et al., *Clinica Chimica Acta.* (2006)). Thus, understanding the exact role of β2-GPI itself or the natural antibodies recognizing β2-GPI in mediating tissue damage may provide effective strategies for preventing reperfusion injury in multiple organs.

Example 2

Administration of Peptides Post-Reperfusion

Figure 13:
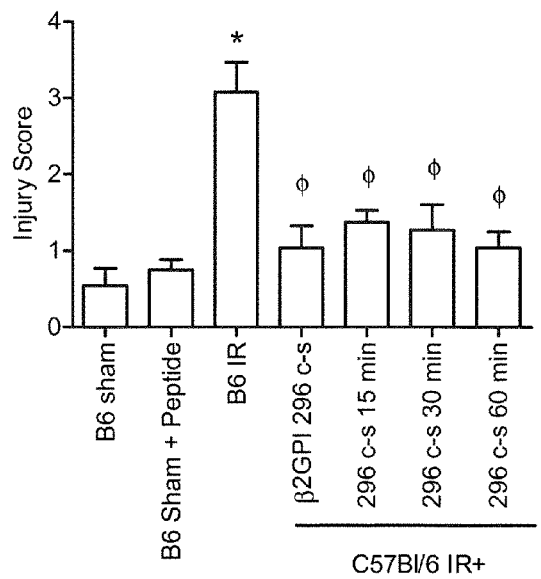
FIG. 13 shows graphs of the injury scores when the peptides were administered post-reperfusion in Example 2.
Figure 13:
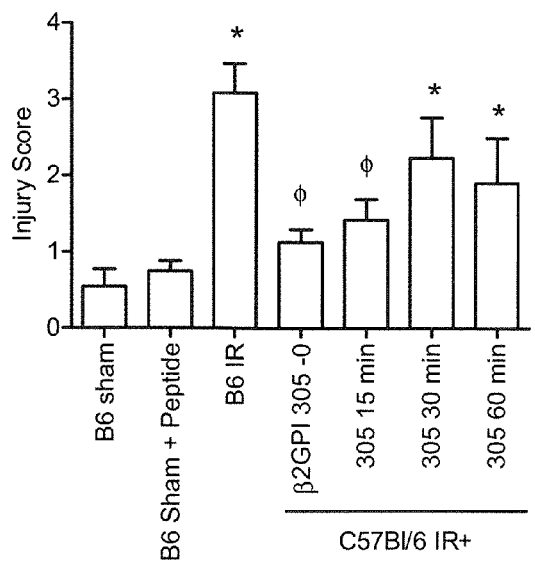

Additional work was carried out using procedures outlined in Example 1, however, β2-GPI peptides 296Cys to Ser or 305 peptides were administered to C57Bl/6 mice subjected to Sham or IR treatment prior to reperfusion, or 15-, 30-, or 60-minutes post-reperfusion. Intestinal injury was scored as described in Example 1 on H&E stained, mid-jejunal tissue sections (75-150 villi per animal). The results are provided in FIG. 13. FIG. 13(A) shows the results of administration of peptide 296Cys-Ser. The results for the administration of peptide 305 are provided in FIG. 13(B). In both graphs, *=p≤0.05 compared to Sham+peptide and Φ=p≤0.05 compared to IR-treated animals not receiving peptides. Each bar is representative of 3-4 animals and each treatment was performed on at least 2 separate days. As can be seen from the data, administration of the peptides after reperfusion was effective for attenuating IR-induced intestinal injury.

Example 3

Administration of Human β2-GPI Whole Molecule to Mice

Figure 14:
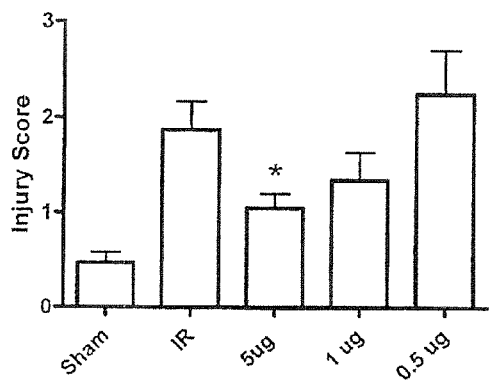
FIG. 14 shows a graph of the injury score when human β2-GPI (whole molecule) was administered to mice subjected to IR or sham treatment in Example 3.

Additional work was carried out using procedures outlined in Example 1, however, a commercially-available human β2-GPI (SEQ ID NO. 15) was administered to C57Bl/6 mice subjected to Sham or IR treatment. The mice were administered N. saline or human β2-GPI dissolved in N. saline at 0.5-μg, 1-μg and 5-μg concentrations, and intestinal injury was subsequently scored, as described in Example 1. The results are shown in FIG. 14, where *=p≤0.05 compared to Sham. Each bar is representative of 3-4 animals and each treatment was performed on at least 2 separate days. As can be seen from the data, human β2-GPI effectively competes with mouse β2-GPI and was effective at attenuating IR-induced intestinal injury in the mice.

Example 4

Additional β2-GPI Peptides for Attenuation of IR Injury

1. Peptides

Smaller β2-GPI peptides were designed and synthesized based upon peptides 296 and 305 from Example 1 above. Peptide p7 contained the consensus sequence for lipid binding found in peptide 296 with the Cys to Ser substitution. Peptides p9 and p11 from peptide 305 also contained the Cys to Ser substitution from peptide 305. Additional forms of p9 were created using D-amino acids (D-p9) or the retro-inverso (defined as peptide sequences reversed) of D-p9 ("Retro-inverso" D-p9). Retro-inverso sequences switch the C- and N-termini directionality of an L-peptide (e.g. the retro-inverso sequence of L-NH$_2$-ABCDEF-OH would be D-NH$_2$—FEDCBA-OH). By inverting the D-sequence, the side-chain groups approximate the position they occupy in the all L-sequence. Further sequences designated as p16 and scrambled p16 were also synthesized. The peptide sequences are provided in Table 3 below. All peptides were generated at the KSU Biochemistry Core Laboratory by solid-phase synthesis with 9-fluorenylmethoxycarbinyl chemistry in the Biotechnology Core Laboratory at Kansas State University as described previously (Iwamoto, T. et al., *Int. J. Peptide Prot. Res.* 43:597-607 (1996)). The peptides were purified by reversed phase HPLC and characterized by matrix-assisted laser desorption time of flight mass spectroscopy. All lyophilized peptides were stored at −20° C. until time of use.

mately 0.5 mL) over a 90-second period (Fleming, S. D. et al., *J. Surg. Res.* 150:196-203 (2008); Hylton, D. J. et al., *Shock* 34:467-474 (2010); Hylton, D. J. et al., *Shock* 35: 134-140 (2011)). Volume of blood to be removed was based on animal weight and ranged from 400 mL to 600 mL (body weight in grams×0.025). The determined blood volume was measured in water and marked on both the collection tubes and the

TABLE 3

β2-GPI Peptide Sequences

| Peptide Name | Sequence | Residue Numbers | MW (Da) |
| --- | --- | --- | --- |
| 296Cys-Ser | H-IHFYSKNKEKKSSYTVEAHSRDGTI-NH2 (SEQ ID NO. 9) | 296-320 | 2925 |
| 305 | H-KKCSYTVEAHCRDGTIEIPSCFKEHS-OH (SEQ ID NO. 10) | 305-330 | 2969 |
| p7 | H-SKNKEKK-NH2 (SEQ ID NO. 11) | 300-306 | 860 |
| p9 | H-SSYTVEAHS-NH2 (residues 3-11 of SEQ ID NO. 12) | 307-315 | 979 |
| p11 | H-KKSSYTVEAHS-NH2 (SEQ ID NO. 12) | 305-315 | 1235 |
| p16 | H-KKSSYTVEAHSRDGTI-NH2 (SEQ ID NO. 19) | 305-320 | 1777 |
| D-p9 | H-SSYTVEAHS-OH with D-amino acids (residues 3-11 of SEQ ID NO. 12) | 307-315 | 979 |
| Retro-inverso D-p9 | H-SHAEVTYSS-OH with D-amino acids (SEQ ID NO. 13) | — | 979 |
| p16 Scrambled | H-DEVHYTTSSSKKARGII-NH2 (SEQ ID NO. 20) | — | 1777 |

2. Experimental Mice

Originally obtained from Jackson Laboratory, C57Bl/6 mice were bred and maintained in the Division of Biology at Kansas State University. Housed in a 12-hour light-to-dark, temperature-controlled room, mice were allowed food and water ad libitum. All mice were kept in specific pathogen free conditions (*Helicobacter* species, mouse hepatitis virus, minute virus of mice, mouse parvovirus, Sendai virus, murine norovirus, *Mycoplasma pulmonis*, Theiler's murine encephalomyelitis virus, and endo- and ecto-parasites). All research was approved by the Institutional Animal Care and Use Committee and conducted in compliance with the Animal Welfare Act and other Federal statutes and regulations concerning animals. All procedures were performed with the animals breathing spontaneously and body temperature maintained at 37° C. using a water-circulating heating pad.

3. Ischemia/Reperfusion Procedure

Ischemia/reperfusion was performed on ketamine/xylazine anesthetized mice as described in Example 1 above. After 2 hours of reperfusion, the mice were euthanized and sera, liver, spleen, and 2 cm sections of the small intestine, approximately 10 cm distal to the gastroduodenal junction, were collected for histological and other analyses. Mice treated with the various β2-GPI peptides underwent the same procedure with i.v. administration of the peptides. Most studies assumed 2 mL total blood volume in a mouse and administered peptides to a final concentration of 40 μM at 5 min prior to ischemia. Dose response studies administered 1-40 μM peptide at 5 min prior to ischemia and time course studies administered 40 μM peptide at 5 min prior to ischemia, and at 15-, 30- or 60-min post-ischemia (i.e., during reperfusion).

4. Hemorrhage

After a 1-week acclimatization period, mice were anesthetized using ketamine (16 mg/kg) and xylazine (80 mg/kg). Mice undergoing hemorrhage were subjected to retro-orbital removal of 30% of the calculated blood volume (approximately capillary tubing used for retro-orbital punctures. This ensured that the correct amount would be withdrawn. A single retro-orbital puncture was sufficient for blood collection. The 2 hour mortality rate was less than 1%. Sham mice were subjected to similar procedures with no blood removal. Mice were randomly assigned to receive 40 uM peptide (80 ng/mouse) in a volume of 80-150 μL, or an equal volume of normal saline. To prevent spontaneous complement activation, all studies were performed in the absence of heparin. At 2 hours post-hemorrhage, mice were euthanized and tissues collected for analysis. Intestinal tissues were formalin fixed for analysis of injury and frozen sections were obtained for immunohistochemistry. Additional intestinal sections were collected for ex vivo eciosanoid generation as described in Example 1.

5. Histology and Injury Scoring

After euthanasia, tissue sections were fixed and stained following the procedures outlined in Example 1. Mucosal injury (SMI) was also graded on a six-tiered scale, as described in Example 1.

6. Ex Vivo Eicosanoid Generation

Total peroxidase, $LTB_4$, $PGE_2$, IL-6, IL-12p40, and IL-12p70 concentrations were determined using the procedures described in Example 1.

7. Macrophage and B Cell Production of Nitric Oxide

C57Bl/6 mice were injected i.p. with 1 mL thioglycollate (4%) 4 days prior to peritoneal lavage. Peritoneal exudate macrophages or the B cell line, LK35.2, were seeded at $2\times10^6$ cells/mL in 24-well or 96-well plates. After macrophage adherence, both cell types were treated with mouse β2-GPI (10 μg/mL) with or without peptide (40 μM). Additional cells were unstimulated as a negative control or stimulated with 10 μg/mL LPS (*E. coli* 055B5) as a positive control. Supernatants were collected 18-20 hours after stimulation and analyzed for nitrite by Griess reagent (Hoffman & Fleming, *Cell Biochem. Funct.* 28:686-694 (2010)) or IL-6 by Milliplex MAP kit (Millipore) following the manufacturer's instructions using a Luminex 200 with xPONENT 3.1 and Analyst software (Millipore).

8. Hypoxia and Immunohistochemistry

Hypoxia was conducted similar to previous studies with the following modifications (Banerjee, S. et al., *Reprod. Biol. Endocrinol.* 7:4 (2009)). Hypoxic cells received degassed, serum-free DMEM and were placed in a hypoxia chamber containing 94% nitrogen, 5% $CO_2$, and 1% $O_2$. Normoxic cells received normal DMEM with 10% FBS in 8% $CO_2$. After 2 hours at 37° C., all cells received fresh medium containing 10% heat-inactivated Rag-1$^{-/-}$ sera and then were incubated under normoxic conditions for 1 hour at 37° C. Cells receiving β2-GPI peptides were administered the peptides (40 µM) during the 2 hours of either hypoxia or normoxia. IgG binding was determined using anti-mouse IgG antibodies (Jackson ImmunoResearch) as previously described (Fleming, S. D. et al., *J. Immunol.* 173:7055-7061 (2004)). Similarly, after Sham or IR, intestinal sections from peptide-treated mice were stained with anti-IgG antibodies to determine antibody deposition. The fluorescence was determined in a blind manner using a Nikon 80i fluorescent microscope and images acquired using a CoolSnap Cf camera (Photometrics) and MetaVue Imaging software (Molecular Devices).

9. Anti-β2-GPI Peptide Competition ELISA

Maxisorp ELISA plates (Fisher) were coated overnight at 4° C. with mouse β2-GPI (400 ng/well). After blocking with 20% FBS for 1 hour, 25 ng/mL FC1 (anti-β2-GPI mAb) mixed with or without 40 µM peptide was added to designated wells for 1 hour at room temp. After washing with PBS-T, peroxidase-conjugated secondary anti-mouse Ig (150 ng/mL) was added for an additional hour. After additional washes with PBS-T, the wells were developed with TMB, stopped with sulfuric acid and $OD_{450}$ determined. Data was analyzed using GraphPad Prism.

10. β2-GPI-IgG Complex ELISA

Complexes were analyzed similar to previously published results (Lee, H. et al., *Mol. Immunol.* 47:972-981 (2010)). Briefly, maxisorp ELISA plates (Fisher) were coated overnight at 4° C. with goat-anti-human β2-GPI and blocked for 2 hours at room temperature with 1% BSA in 0.05% PBS-Tween. Intestinal homogenates (1.2 ng/well) from mice subjected to Sham or IR treatment in the presence or absence of peptide were added and maintained overnight at 4° C. After washing three times with PBS-Tween, the complexes were incubated with HRP-labeled anti-mouse IgG detection antibodies (Jackson ImmunoResearch) for 2 hours at room temperature. Complexes were detected with TMB as described previously (Fleming, S. D. et al., *J. Surg. Res.* 150:196-203 (2008)).

11. Melanoma Model

The mouse melanoma cell line, B16-F10 (ATCC CRL-6475), was cultured in DMEM supplemented with 10% fetal bovine serum at 8% $CO_2$ until confluent. C57Bl/6 mice were injected subcutaneously with $2 \times 10^6$ cells mixed 1:1 in matrigel (BD Biosciences) and tumor growth was evaluated daily for up to 10 days using calipers. Some mice received 40 µM peptide daily for the first 4 days and then every other day until termination of the study. Control mice received N. saline. At the end of the study, the tumors were dissected and tumor volume determined by saline displacement. Photomicrographs (10×) of representative B16-F10 tumors extracted from C57Bl/6 wildtype mice were taken with a Nikon CoolSnap CF camera and an Olympus SZ61 microscope.

The study was repeated using additional C57Bl/6 mice, which were injected subcutaneously with $2 \times 10^6$ cells mixed with matrigel (above) 6-10 days before tumor excision. Peptide treated mice received 40 µM peptide 296Cys-Ser on days 1, 2, 3, 4, 6, and 8 after injection (n=2-5 animals/group) or days 3, 5, 7, 9 or only on days 4, 6, and 8. At the end of the study, the tumors were excised, measured, and volume was determined by aqueous displacement. Tumors were cut in half longitudinally with one half homogenized in Trizol for RNA and the other placed in OCT for histological analysis. Both halves were snap frozen and stored at −80° C. until used.

mRNA was isolated from the tumor samples that were homogenized in Trizol. The concentration of mRNA was evaluated by nanodrop and the purity by bioanalyzer. cDNA was then synthesized using random primers with the Quanta cDNA synthesis kit. Real-time PCR was then performed on a 1:100 dilution of cDNA for 18s rRNA. After 3 min denaturing at 95° C., the real-time PCR reaction consisted of 50 cycles (of 10 sec at 95° C., 20 sec at 58° C., and 10 sec at 72° C.), followed by a melt curve increasing at intervals of 0.5° from 60° C. to 95° C. RT-PCR was also performed on cDNA samples for CD31 and endoglin which are endothelial markers of angiogenesis. Fold change of each gene was determined by subtracting 18s for normalization of RNA and fold change was determined by comparing to original cells which were set to 1. Primers were obtained from Integrated DNA Technology (Coraville, Iowa) and sequences are in the table below.

OCT cryopreserved tumor sections were cut and stained similar to intestinal sections in Example 1. CD31 and Pan-endothelial expression was detected by FITC conjugated rat anti-mouse CD31 or pan-endothelial antibodies (Biolegend, San Diego, Calif.). Each experiment contained serial sections stained with the appropriate isotype control antibodies. All slides were mounted with ProLong Gold (Invitrogen) and images were obtained and analyzed as described in Example 1.

12. Breast Cancel Model

Ten male Fvb/N-Tg(MMTV-PyVT)634Mul/J mice were generously donated by T. A. Nguyen and maintained under 12 h light/dark cycles at Kansas State University, Division of Biology (Manhattan, Kans.). These mice are Her2$^+$ Estrogen receptor α/β$^+$, Progesterone receptor$^+$, p53$^+$ animal models that spontaneously develop breast cancer. All mice were allowed access to food and water ad libitum and maintained under specific pathogen free conditions. Research was conducted in compliance with the Animal Welfare Act and other federal statutes and regulations relating to animals and experiments involving animals and was approved by the Institutional Animal Care and Use Committee.

Mice were observed 3 times a week until tumors were palpable. Randomly, mice were assigned to receive treatment with N. Saline or peptide 296c-s. Each peptide treated mouse received β2-Glycoprotein 1 Peptide 296c-s (40 µM) by retro-orbital injection three times a week for 7 additional weeks. N. Saline treated mice received the same volume (80 µL) of 0.15M normal saline retro-orbitally three times a week as a control group.

Tumors were measured by hand with calipers three times a week for 7 weeks after the start of injection. After 7 weeks, the mice were briefly anesthetized using isofluorene followed by cervical dislocation euthanization and the tumors were harvested. The tumors were measured volumetrically. In addition, photomicrographs were taken with a Nikon CoolSnap CF camera and an Olympus SZ61 microscope. The tumors were cut into halves and then the halves were either homogenized in 1 mL of Trizol or placed in OCT compound, snap frozen in liquid nitrogen and stored at −80° C. until needed.

mRNA was isolated from the tumor samples that were homogenized in Trizol. The concentration of mRNA was evaluated by nanodrop and the purity by bioanalyzer. cDNA was then synthesized using random primers with the Quanta cDNA synthesis kit. RT-PCR was then performed on a 1:100 dilution of cDNA for 18s rRNA. After 3 min denaturing at 95° C., the real-time PCR reaction consisted of 50 cycles (of 10 sec at 95° C., 20 sec at 58° C., and 10 sec at 72° C.), followed by a melt curve increasing at intervals of 0.5° C. from 60° C. to 95° C. RT-PCR was also performed on cDNA samples for CD31 and VEGF which are endothelial markers of angiogenesis. After subtracting 18s Ct values, peptide treated dCt values were normalized to saline treated samples and fold change calculated as ddCt. Primers were obtained from Integrated DNA Technology (Coraville, Iowa) and sequences are in the table below.

Figure 15:
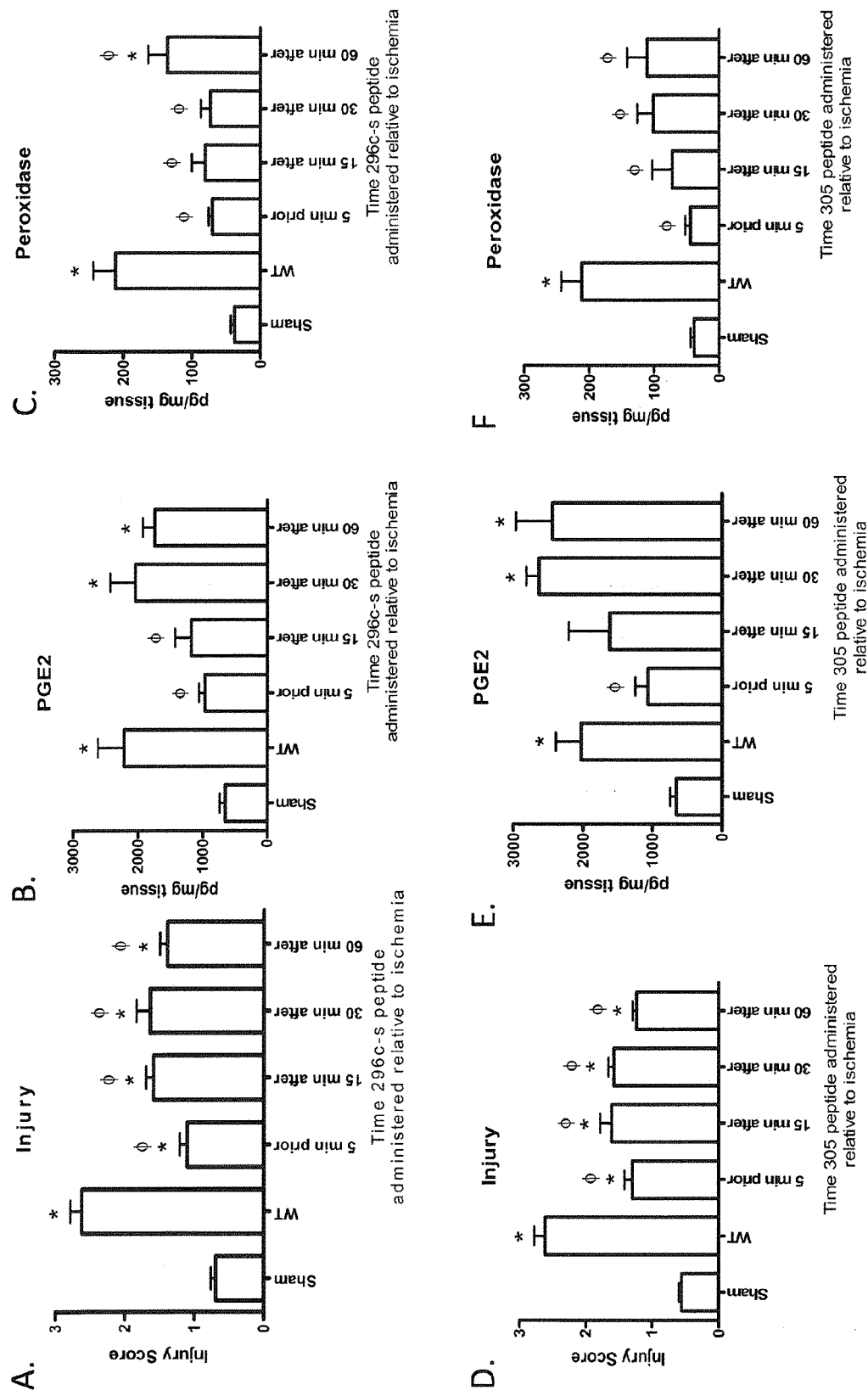
FIG. 15 shows graphs of the injury score, PGE2 and peroxidase concentrations in mice subjected to IR or sham treatment in the presence or absence of peptides 296Cys-Ser and 305, administered before or after IR, from Example 4.

IR-induced injury, which is not possible in most clinical situations. Therefore, we determined the optimal time of peptide administration. The results are provided in FIG. 15 where the values are represented as pg/mg of intestinal protein, *=p≤0.05 compared to Sham+peptide, and Φ=p≤0.05 compared to IR-treated mice not receiving peptides. Each bar is representative of 2-8 animals and each treatment was performed on at least 2 separate days. As indicated in FIGS. 15(A), (D), both peptides appear to be effective in preventing intestinal injury when administered at either 5- or 15-min post-reperfusion in this 2-hour assay. In addition, treatment at both 30 min and 60 min post-reperfusion significantly decreased intestinal injury. We also examined prostaglandins E2 (PGE2) (FIGS. 15(B), (E)) and peroxidase (FIGS. 15(C), (F)) production as markers of the

TABLE 4

Real time PCR Primer sequences

| Gene | | Primer Sequence | Temperature |
|---|---|---|---|
| 18S | Forward | GGTTGATCCTGCCAGTAGC (SEQ ID NO. 21) | 58° C. |
| | Reverse | GCGACCAAAGGAACCATAAC (SEQ ID NO. 22) | |
| Endoglin | Forward | CTTCCAAGGACAGCCAAGAG (SEQ ID NO. 23) | 56° C. |
| | Reverse | GTGGTTGCCATTCAAGTGTG (SEQ ID NO. 24) | |
| CD31 | Forward | TGCTCTCGAAGCCCAGTATT (SEQ ID NO. 25) | 56° C. |
| | Reverse | TGTGAATGTTGCTGGGTCAT (SEQ ID NO. 26) | |
| VEGF | Forward | AGAGCAACATCACCATGCAG (SEQ ID NO. 27) | 54° C. |
| | Reverse | TTTCTTGCGCTTTCGTTTTT (SEQ ID NO. 28) | |

13. Statistical Analysis

Data are presented as mean±SEM and significance (p<0.05) determined by one-way ANOVA with Newman-Keuls post hoc analysis (GraphPad/Instat Software).

14. Results a. Peptides 296Cys-Ser and 305 Attenuate IR-Induced Tissue Peroxidase Production Previous studies indicated that β2-GPI is critical to IR-induced tissue damage (Fleming, S. D. et al., *J. Immunol.* 169:2126-2133 (2002)); Fleming, S. D. et al., *J. Immunol.* 173:7055-7061 (2004)) and that peptides derived from β2-GPI inhibit complement deposition, PGE2 production and intestinal damage in response to IR. However, inhibition of neutrophil infiltration and activation also prevents intestinal damage (Hernandez, L. A. et al., *Am. J. Physiol.* 253: H699-H703 (1987)). Therefore, we examined the ability of the peptides to inhibit neutrophil peroxidase activation when administered prior to IR. Similar to previous results, treatment with peptides 296Cys-Ser and 305 significantly attenuated peroxidase production. In contrast, treatment with control peptides or peptide 322 resulted in intestinal peroxidase concentrations similar to saline treated animals. Thus, β2-GPI peptides attenuate intestinal damage via multiple mechanisms including neutrophil activation.

b. Therapeutically Administered Peptides 296Cys-Ser and 305 Protect from IR-Induced Damage Previous studies indicated that both peptide 296Cys-Ser and peptide 305 prevented intestinal ischemia/reperfusion (IR)-induced tissue injury and prostaglandin E2 (PGE2) production. However, the peptides were administered prior to IR-induced injury, which is not possible in most clinical situations. Therefore, we determined the optimal time of peptide administration. The results are provided in FIG. 15 where the values are represented as pg/mg of intestinal protein, *=p≤0.05 compared to Sham+peptide, and Φ=p≤0.05 compared to IR-treated mice not receiving peptides. Each bar is representative of 2-8 animals and each treatment was performed on at least 2 separate days. As indicated in FIGS. 15(A), (D), both peptides appear to be effective in preventing intestinal injury when administered at either 5- or 15-min post-reperfusion in this 2-hour assay. In addition, treatment at both 30 min and 60 min post-reperfusion significantly decreased intestinal injury. We also examined prostaglandins E2 (PGE2) (FIGS. 15(B), (E)) and peroxidase (FIGS. 15(C), (F)) production as markers of the inflammatory response (Moses, T. et al., *J. Leukoc. Biol.* 86:971-980 (2009); Pope, M. R. et al., *Mol. Immunol.* 48:356-364 (2010)).

Figure 16:
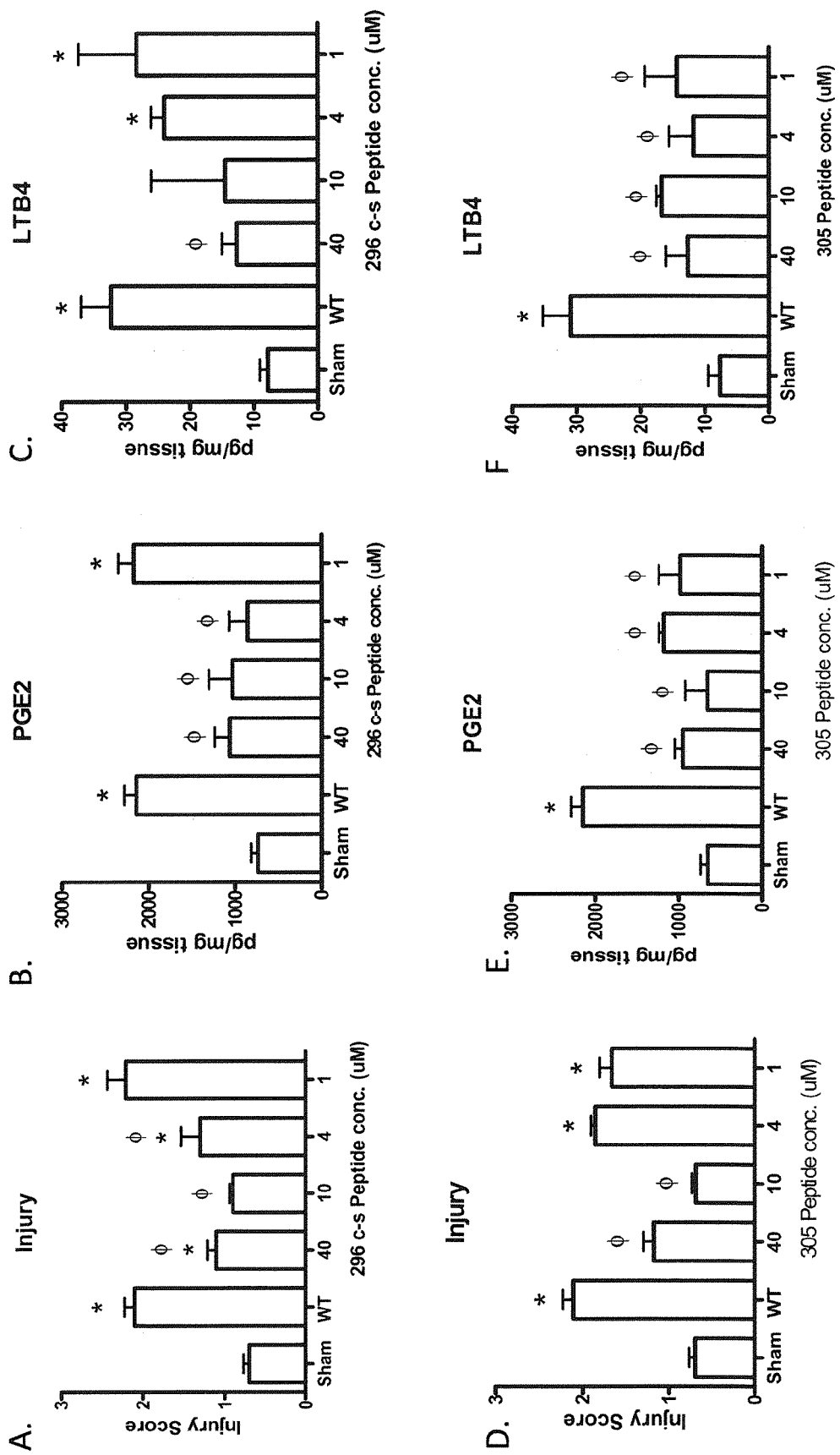
FIG. 16 shows graphs of the injury score, PGE2 and LTB4 concentrations in mice subjected to IR or shame treatment in the presence or absence of varying concentrations of peptides 296Cys-Ser and 305, administered 5 minutes before IR, from Example 4.

The data demonstrates that both peptides attenuated intestinal injury even when administered at 60 min post-reperfusion. In addition, total peroxidase production by the intestinal tissues was significantly decreased when either peptide was administered up to 60 min post-reperfusion. As eicosanoids, leukotriene B4 (LTB4) and prostaglandins E2 (PGE2) play roles in IR-induced intestinal inflammation, we also evaluated these molecules in peptide-treated mice. Treatment with peptides 296Cys-Ser and 305 attenuated PGE2 production when administered at 15 min post-reperfusion. After treatment with peptide 305, we observed a similar time course of LTB4, a chemotactic factor for inflammatory cells. In contrast, IR-induced LTB4 was significantly inhibited by peptide 296Cys-Ser at all time points examined. These results suggest that both peptides may be appropriate therapeutics for IR-induced injury.

c. Peptides 296Cys-Ser and 305 Attenuate IR-Induced Injury in a Dose Dependent Manner To determine the optimal dose of each peptide when administered prior to IR, we treated at least 3 mice with multiple concentrations of peptides 296Cys-Ser or 305. The results are shown in FIG. 16, where the values are represented as pg/mg of intestinal protein, *=p≤0.05 compared to Sham+ peptide, and Φ=p≤0.05 compared to IR treatment animals not receiving peptides. Each bar is representative of 2-8 animals and each treatment was performed on at least 2 separate days.

As indicated in FIG. 16, 10 μM treatment of either peptide optimally attenuated injury and PGE2 production. Only peptide 296Cys-Ser also attenuated intestinal damage at 4 μM. In addition, similar concentrations of each peptide attenuated intestinal peroxidase and PGE2 production. These studies indicated that both peptides, 296Cys-Ser and 305, remain effective when administered at lower concentrations than previously reported.

d. Multiple Short Peptides Attenuate IR-Induced Tissue Damage and Inflammation

Figure 17:
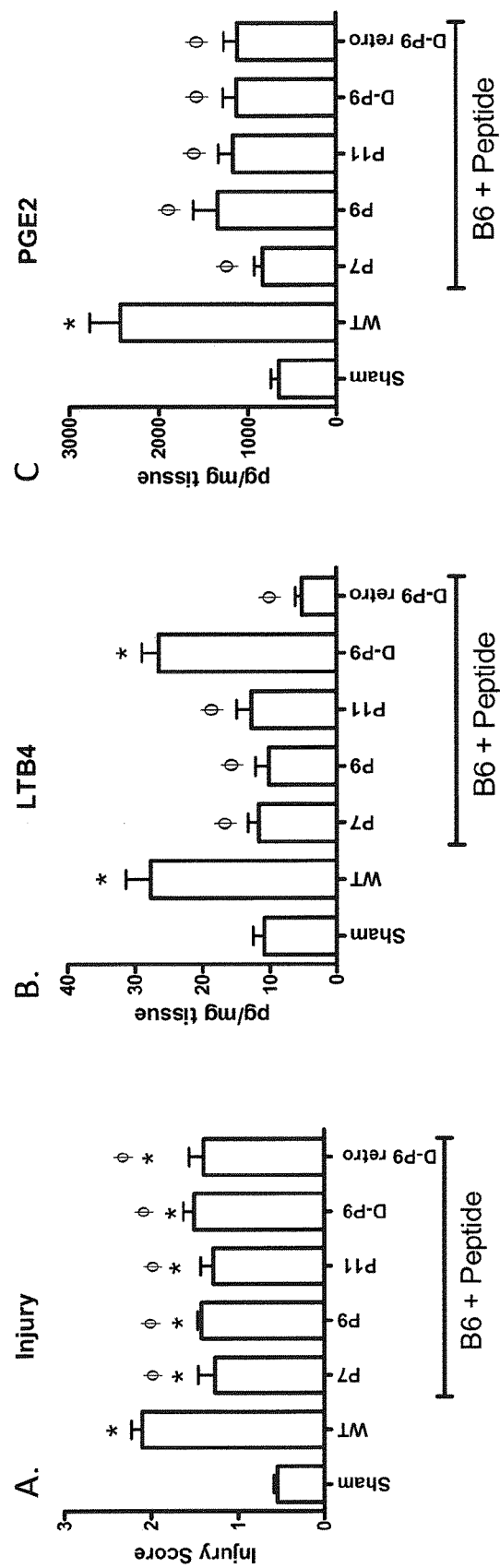
FIG. 17 shows graphs of the injury score, PGE2 and LTB concentrations in mice subjected to IR or sham treatment in the presence or absence of several different peptides administered before IR from Example 4.

As both peptides 296 and 305 contain approximately 25 amino acids, we examined smaller sequences to determine the specific sequences which contain equivalent inhibitory activity. As such, we identified three peptides containing 7-11 amino acids which provided intestinal protection from IR-induced injury and inflammation. Similar to the long peptides, these short peptides attenuated IR-induced intestinal injury when administered preventively. The short peptides (40 μM) were administered i.v. to wildtype, C57BL/6 mice 5 min prior to ischemia. The results are shown in FIG. 17, where the values are represented as pg/mg of intestinal protein, *=p≤0.05 compared to Sham+peptide, and Φ=p≤0.05 compared to IR treatment animals not receiving peptides. Each bar is representative of 2-8 animals and each treatment was performed on at least 2 separate days.

As indicated in FIG. 17, peptide treatment resulted in significantly decreased intestinal epithelial injury compared to similar mice subjected to IR only. Importantly, none of the mice treated with the short peptides were significantly different from mice treated at the same time point, with a similar concentration of peptide 296Cys-Ser (data not shown), which was confirmed to attenuate injury. Similar to the injury score, the intestines of all peptide-treated mice secreted similar concentrations of LTB4 without regard to Sham or IR treatment. All concentrations were significantly different from IR treated mice and were similar to that found in mice subjected to Sham treatment. Interestingly, all peptides attenuated IR-induced, PGE2 production but only peptide p7 returned PGE2 concentrations to those found in Sham treated animals. These data suggest that the shorter peptides may provide therapeutic efficacy similar to or even better than the larger peptides. Having small active peptide sequences will also lower the cost of production, purification and characterization. Also on a per gram basis the shorter peptides will have higher activity since there are more molecules of the smaller peptides per unit weight.

e. D-Amino Acid Replacement and Retro-Inverso D Forms of Peptide p9 in Intestinal IR-Induced Damage and Complement Deposition Mammalian proteins consist almost exclusively of L-amino acids. Due to changes in the location of the amino acid side groups, proteins consisting of D amino acid sequences of most bioactive peptides are inactive; however, they are also not appreciably degraded by proteolytic enzymes. We hypothesized that β2-GPI peptides containing all D amino acids would not protect against IR-induced damage while the retro-inverso of the amino acid sequence of the D-amino acid peptide should provide protection and also have a longer in vivo half-life. Thus, prior to IR, we treated mice with peptides D-p9 (p9 synthesized with D-amino acids) and Retro-inverso D-p9 (D-p9 in the retro-inverso sequence). Surprisingly, treatment with either peptide D-p9 or peptide Retro-inverso D-p9 attenuated IR-induced intestinal injury and PGE2 production similar to peptide p9 treatment (FIG. 17). However, only p9 and Retro-inverso D-p9 attenuated LTB4 production in response to IR, whereas D-p9 did not.

Figure 18:
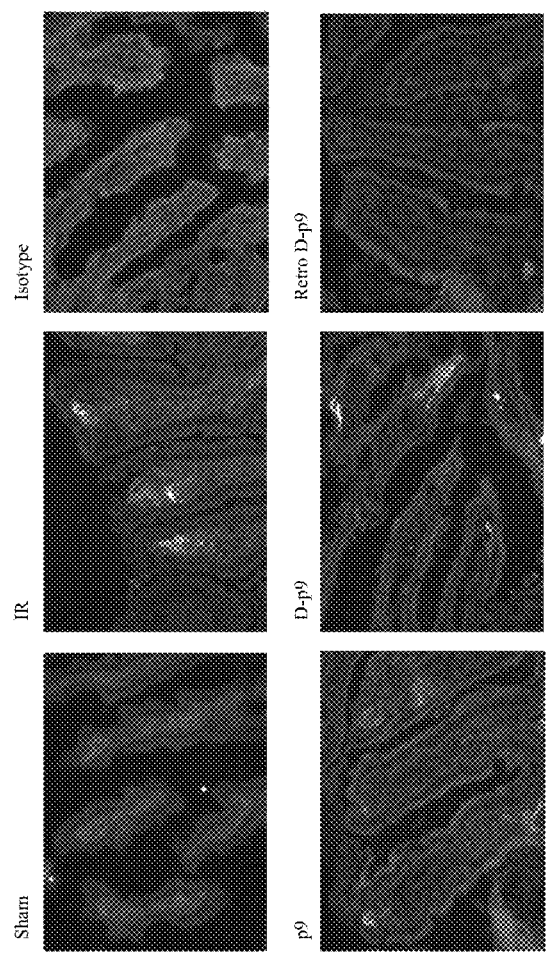
FIG. 18 shows images of tissue sections stained for C3 production from Example 4.
Figure 19:
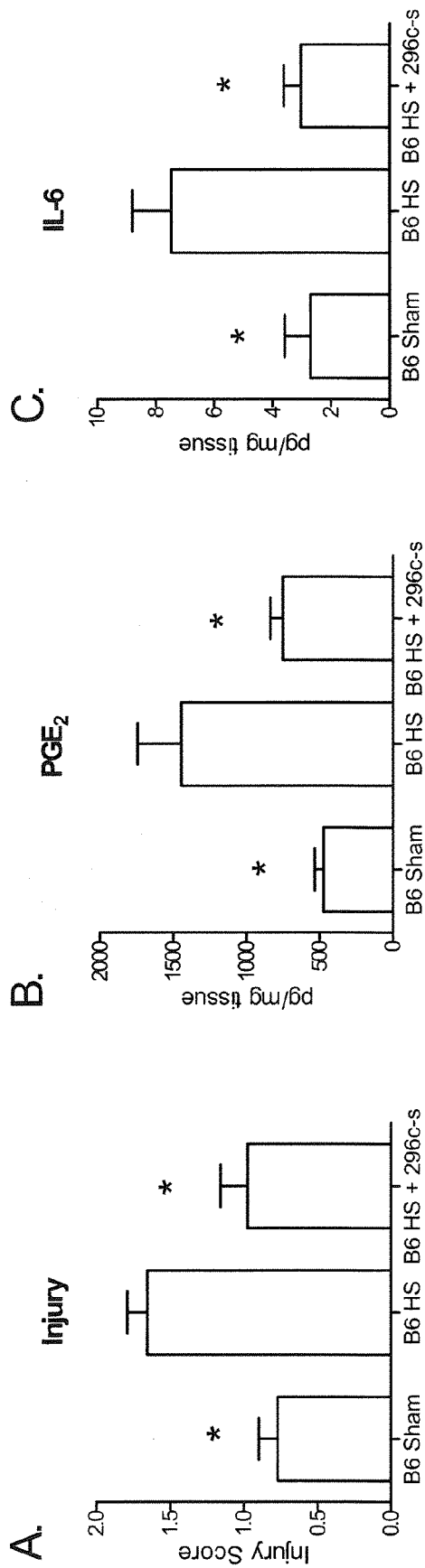
FIG. 19 is a graph showing the injury and inflammation of mice subjected to hemorrhage in Example 4 in the presence of absence of peptide 296Cys-Ser; the data indicates that peptides inhibit not only damage (which is subjective) but also inflammation (which is quantitative)
Figure 20:
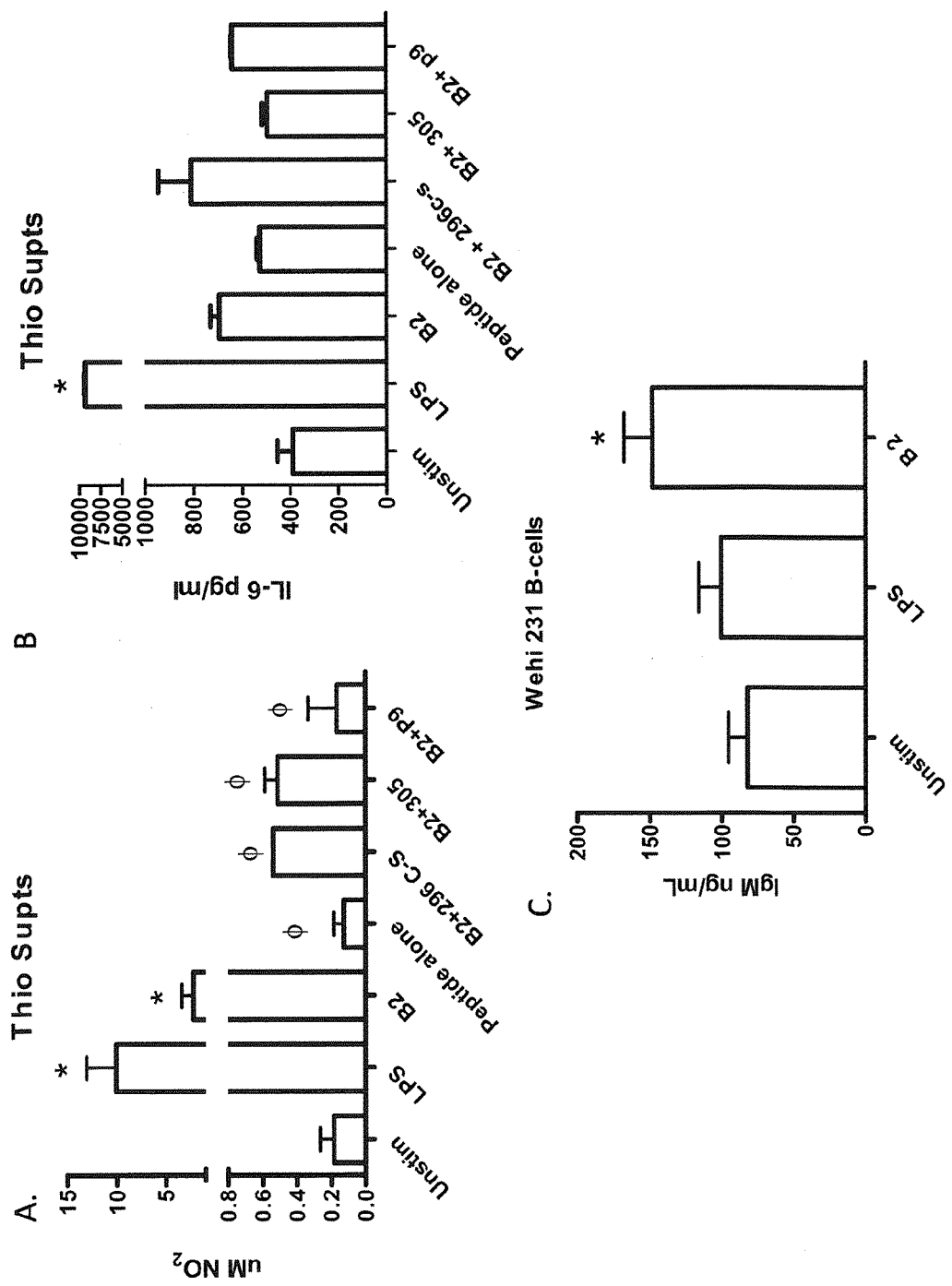
FIG. 20 shows graphs of the results of ex vivo β2-GPI-stimulated macrophage secretions from Example 4.

Complement component, C3 is rapidly deposited and required for IR-induced intestinal damage. Therefore, we also examined the ability of peptides to attenuate C3 deposition after IR. The results are provided in FIG. 18, which shows representative (3-4 animals) intestinal sections stained for C3 deposition in at least 3 independent experiments. As indicated in FIG. 18, intestinal IR induced C3 deposition in untreated mice was significant, while mice treated with p9 had significantly less deposition, and few to no C3 deposits were found in mice treated with Retro-inverso D-p9. Together, these data suggest that Retro-inverso D-9 may have an extended in vivo half-life, while maintaining similar function to peptide p9. In addition, an increase in half-life has the added benefit of decreasing cost of using this peptide in the clinic.

f. Peptide Treatment Attenuates Hemorrhage Induced Intestinal Damage and Inflammation During severe blood loss or hemorrhage, the body shunts the remaining blood volume to vital organs such as the heart, lungs and brain. This process can result in an ischemic intestine, which is reperfused once blood flow resumes. Similar to IR-induced intestinal damage, hemorrhage induces intestinal damage that is mediated by complement activation (Fruchterman, T. M. et al., Surgery 124:782-792 (1998); Rajnik, M. et al., Shock 17:322-328 (2002); Szebeni, J. et al., Shock 20:347-355 (2003)). We subjected wildtype, C57Bl/6 mice with or without peptide treatment to blood loss in the absence of trauma to determine if the peptides attenuate hemorrhage-induced intestinal damage and PGE2 and IL-6 production as measures of inflammation. The results are shown in FIG. 19, where *=p≤0.05 compared to Sham and Φ=p≤0.05 compared to hemorrhage+PBS treated animals. Each bar is representative of 3-10 animals. As indicated in FIG. 19, hemorrhage-induced intestinal damage and inflammation was significantly lower when mice were treated with peptide 296Cys-Ser after blood loss. These data suggest that the peptides will be therapeutic for hemorrhage due to trauma, as well as hemorrhagic stroke.

g. Ex Vivo β2-GPI Stimulated Macrophage Secretions are Inhibited by Peptide Administration Recent evidence suggests that β2-GPI binds the pattern recognition receptor, TLR2 that is prominent on macrophages. (Alard, J. E. et al., J. Immunol. 185:1550-1557 (2010)). We hypothesized that β2-GPI may stimulate cytokine production through TLR2 and that the β2-GPI derived peptides would either inhibit or stimulate the cytokines. Thioglycollate-elicited macrophages were stimulated with β2-GPI with or without peptide, LPS as a positive control, or left unstimulated for 18 hours. The supernatants were collected and analyzed for cytokines and nitric oxide. The results are shown in FIG. 20, where *=p≤0.05 compared to unstimulated cells and Φ=p≤0.05 compared to β2-GPI stimulation. Each bar is representative of 2-7 replicates. As indicated in FIG. 20, β2-GPI stimulated IL-6 and nitric oxide although significantly less than that stimulated by LPS. Importantly, peptides 296Cys-Ser, 305 and p9 each significantly attenuated β2-GPI-induced nitric oxide production. However, only peptide 305 attenuated β2-GPI induced IL-6 production. These data suggest the peptides may be useful in treating additional macrophage-mediated diseases.

h. Angiogenesis and Vascularization is Attenuated by Peptide 296Cys-Ser

Figure 21:
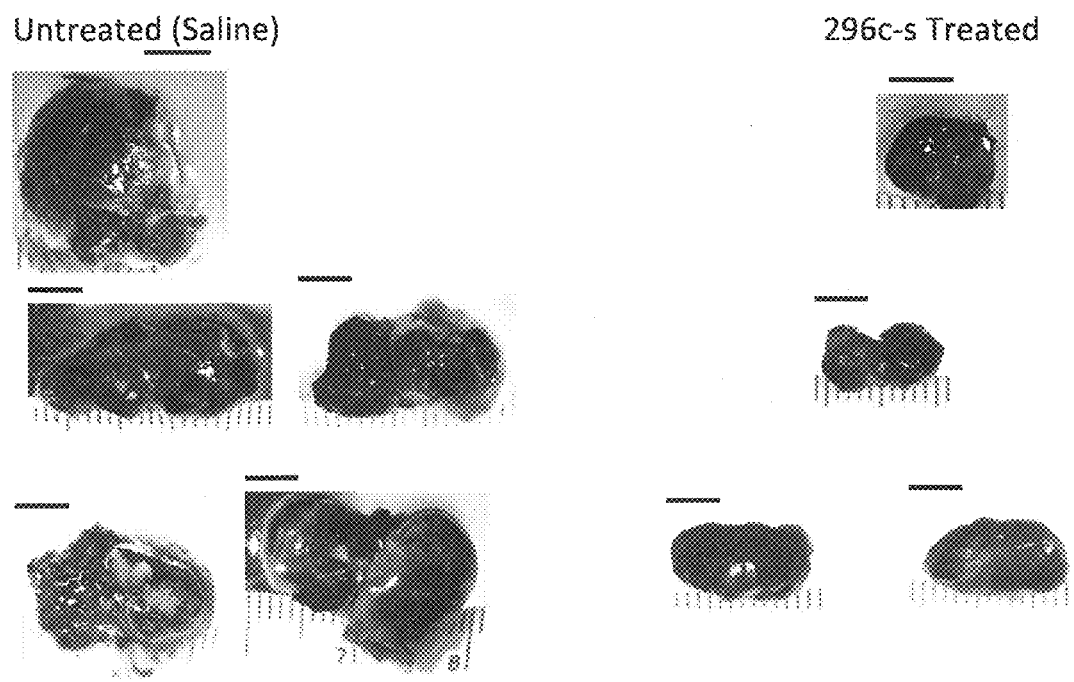
FIG. 21 shows photomicrographs of mice melanomas harvested from mice treated with or without peptide 296Cys-Ser in Example 4.
Figure 22:
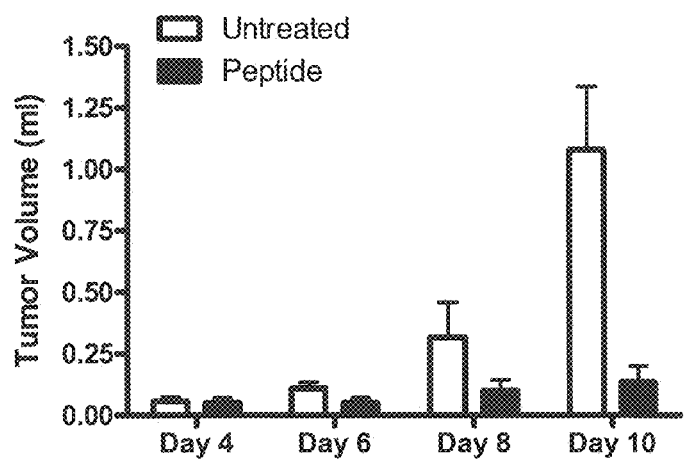
FIG. 22 shows a graph of the results of tumor volume of mice injected to melanoma cells from Example 4 in the presence or absence of peptide 296Cys-Ser.

Hypoxic melanoma and other tumors require vascularization to obtain nutrients and oxygen. To determine if β2-GPI derived peptides inhibit angiogenesis, we injected mice subcutaneously with $2 \times 10^6$ B16-F10 mouse melanoma cells in the presence or absence of peptide 296Cys-Ser. All mice injected with cells in the absence of peptide developed tumors by day 8 which were 0.7-1.3 cm in external size, displaced 0.1-0.5 mL normal saline and appeared vascularized. In contrast, the tumors of 2 mice injected with melanoma cells and peptide 296Cys-Ser were 0 and 0.7 cm in external size, respectively, displaced only 0-0.1 mL normal saline, and neither tumor appear vascularized. In the repeat study, mice receiving peptide 296Cys-Ser had significantly decreased tumor growth and volume as compared to untreated mice. FIG. 21 shows photomicrograph images of the harvested tumors, where the black line next to each image indicates 0.5 cm measurement for reference. The images demonstrate that the results were fairly consistent for all mice. The data demonstrates that the peptides attenuate tumor angiogenesis as well as tumor growth (see FIG. 22).

Figure 23:
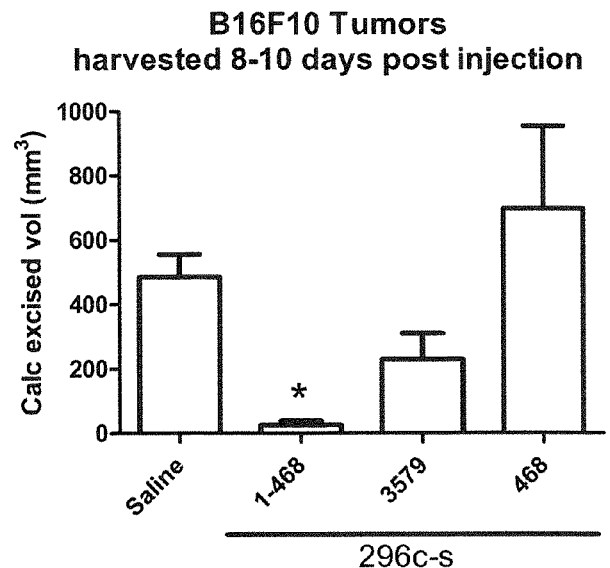
FIG. 23 shows a graph of the tumor volume of melanomas harvested from the treated or control mice in Example 4.

To determine the required treatment schedule, additional mice were injected with B16F10 tumor cells and treated with saline or peptide on days 1, 2, 3, 4, 6, and 8 or treated on days 3, 5, 7, and 9 or treated on days 4, 6, and 8. As indicated in FIG. 23 treatment on days 3, 5, 7, and 9 or 1-4, 6, and 8 attenuated tumor growth where * indicates p<0.05 compared to saline. However, early treatment (days 1-4, 6, 8) of this aggressive tumor prevented growth and in 3 of 7 animals, the tumor was either not present or had significantly diminished from the day of injection.

Figure 24:
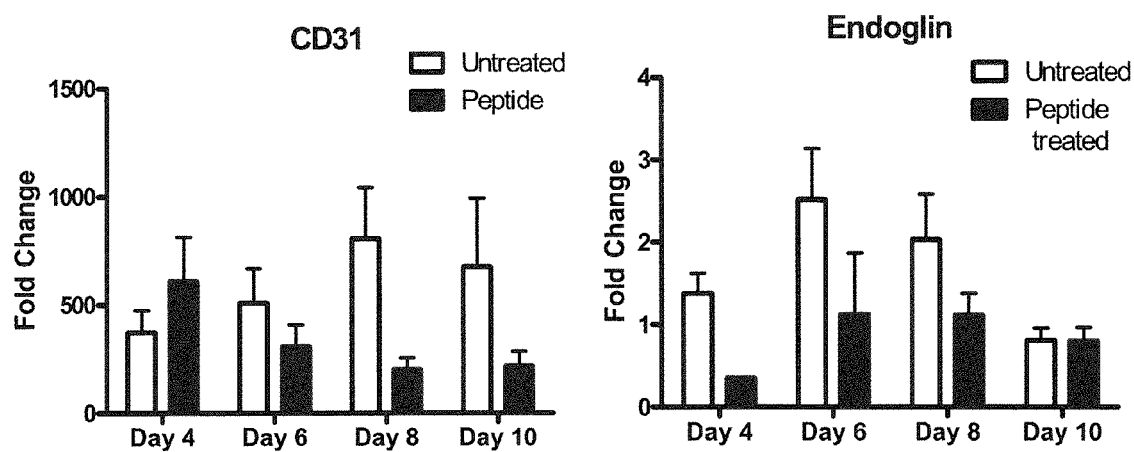
FIG. 24 shows graphs of the data indicating that peptide treatment decreases CD31 and Endoglin RNA expression. As a marker of vascularity, endoglin and CD31 RNA expression was evaluated by qRT-PCR and is reported as fold change compared to cultured B16F10 melanoma cells set as 1. Each bar represents the mean±SEM of 4-5 tumors.
Figure 25:
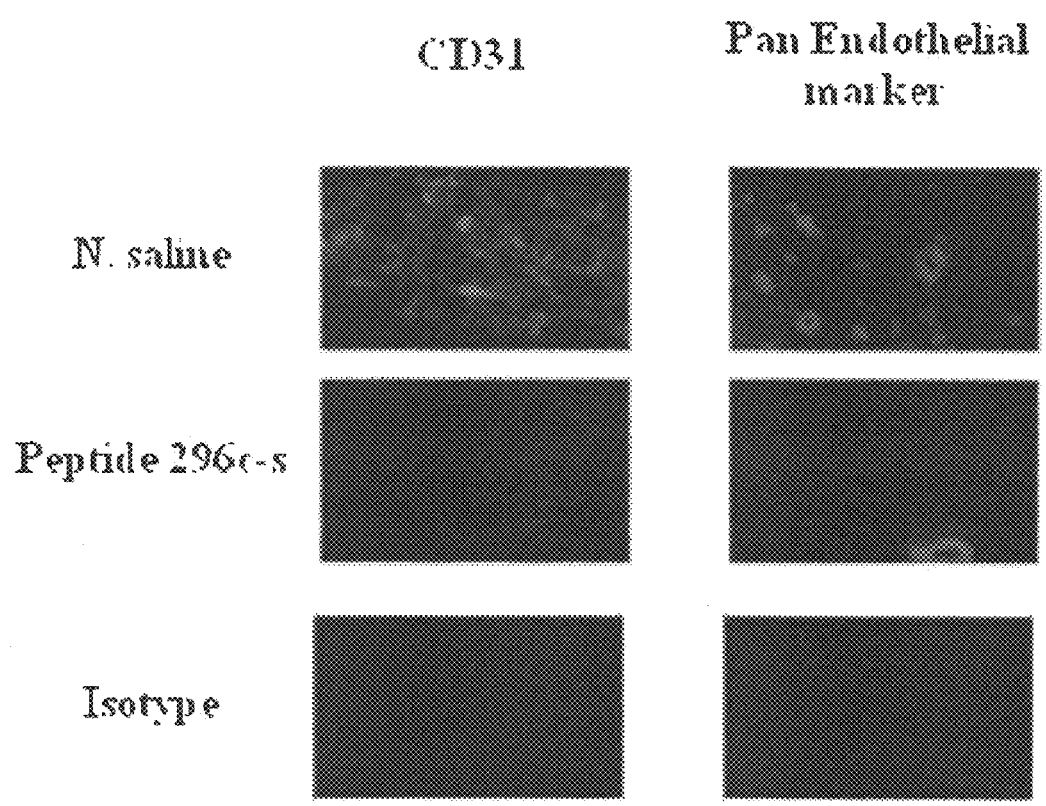
FIG. 25 shows images of tissues stained for CD31 expression to indicate endothelial junctions and with a pan-endothelial antibody to identify small vessel formation. The photomicrographs (200×) are representative of 3 experiments with 4-5 fields per slide and were taken with a Nikon CoolSnap CF camera and an Olympus SZ61 microscope.

Angiogenic markers, endoglin and CD31, are also down regulated in tumors from peptide treated mice, as shown in FIGS. 24 and 25. As the saline treated tumors appeared significantly more vascularized, we examined the RNA expression of angiogenic markers, endoglin and CD31. As part of the TGF-β receptor complex, endoglin is expressed on newly formed blood vessels in vivo, and therefore is a marker for new or immature endothelial cells. (Perez-Gomez, et al., *Sci. World J.* 10:2367-2384 (2010)). CD31 (formerly named platelet endothelial cell adhesion molecule-1 (Pecam-1) is found at the intercellular junctions of endothelial cells and is increased during angiogenesis (Woodfin, et al., *AHA Journal.* 27:2514-2523 (2007)). As indicated in FIG. 24, where each bar represents the mean±SEM of 4-5 tumors, both markers increased in saline-treated tumors although each was expressed in a distinct time course. In contrast, peptide treatment on days 1-4, 6, and 8 attenuated both CD31 and endoglin expression within the tumors. Similarly, protein expression of both endothelial markers was decreased as demonstrated in FIG. 25, which shows the average of 4-5 photos/tumor from 3 animals per treatment group. Immunohistochemistry demonstrated that although an occasional large vessel was present in peptide treated tumors, saline treated tumors contained significantly more small, new vessels. These data suggest that peptide 296c-s attenuates angiogenesis in the B16F10 melanoma model.

Figure 26:
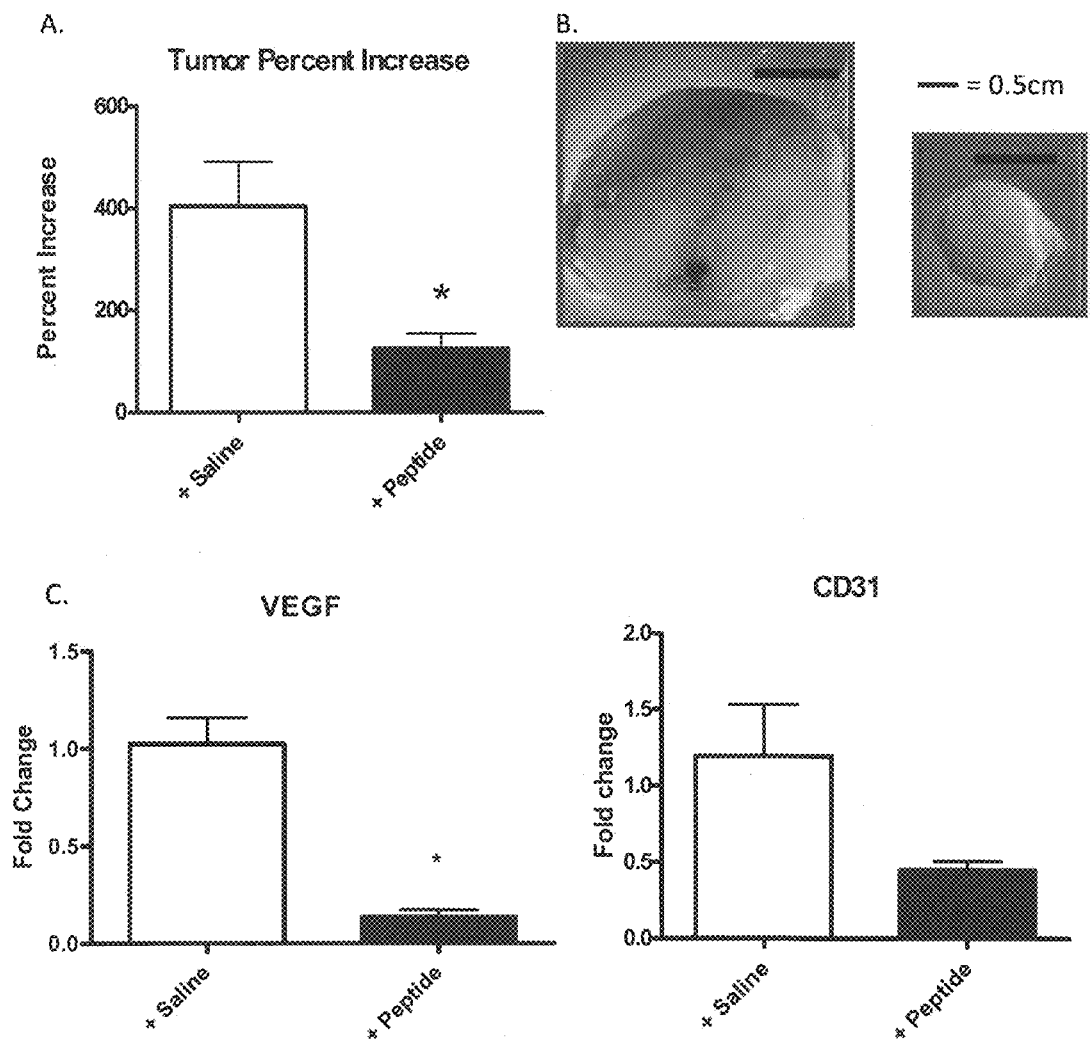
FIG. 26 shows (A) a graph of tumor growth in the mice in Example 4, where each bar represents mean+/−SEM for 4 to 6 animals with 7 tumors for saline treated and 8 tumors for peptide treated. * indicates significant difference (p<0.05) from saline treated to peptide treated; (B) Photomicrographs of harvested tumors. Images are representative of 4 to 6 animals; and (C) graphs of cDNA analysis for CD31, VEGF, and Endosialin expression by realtime PCR. Each bar represent mean+/−SEM. N=4-5 for saline treated and N=3 for peptide treated. * indicates significant difference (p<0.05) from saline treated to peptide treated.

In a spontaneous mouse model of mammary tumors, male mice were treated with or without peptide after detection of a palpable tumor. Tumor expressing mice were treated 3 times per week for 7 weeks. The percent tumor growth compared to initial measurements was determined and is presented in FIG. 26A. Tumor growth was significantly decreased where * indicates p<0.05 compared to saline treated tumor growth. Tumors in FIG. 26B are representative of tumors identified in N. Saline and peptide 296c-s treated mice. To examine angiogenesis, RNA expression of CD31 and Vascular Endothelial Growth Factor (VEGF) were examined. As described above, CD31 marks vascular junctions. VEGF induces angiogenesis, inhibits tumor cell apoptosis and is associated with melanoma metastasis (Palmer, et al., *Mayo Clin Proc* 86:981-990 (2011)). After subtracting 18s Ct values, peptide treated dCt values were normalized to saline treated samples and fold change calculated as ddCt. As indicated in FIG. 26C, RNA for each marker was significantly decreased compared to saline treated animals, where * indicates p<0.05 compared to saline treated tumors. Together, these data suggest that peptide 296c-s may therapeutically inhibit tumor growth and angiogenesis.

i. β2-GPI Derived Peptides May Attenuate Damage in Additional Modes of Tissue Damage β2-GPI plays a role in other forms of complement mediated tissue damage including anti-phospholipid syndrome, myocardial infarction, stroke, thermal injury, heat stroke, macular degeneration, and ocular vaso-occlusive disease (Conti, F. et al., *Clin. Exp. Immunol.* 132:509-516 (2003); de Zwaan, C. et al., *Am. J. Card. Drugs* 3:245-251 (2003); Costa, C. et al., *Brain Res.* 1100:142-151 (2006); Montalvo, V. et al., *Curr. Eye Res.* 32:917-922 (2007); Fleming, S. D. et al., *J. Appl. Physiol.* 92:2600-2607 (2002); Fleming & Tsokos, *Modern Therapeutics in Rheumatic Diseases*, Humana Press 443-452 (2000)). The general mechanism of β2-GPI in most clinical situations involves serum β2-GPI binding to exposed lipids, TLR2, TLR4 or annexin II followed by antibody binding and complement activation (Cockrell, E. et al., *Lupus* 17:943-951 (2008); Alard, J. E. et al., *J. Immunol.* 185:1550-1557 (2010); Zhou, H. et al., *Clin. Exp. Immunol.* 163:189-198 (2011)).

Figure 27:
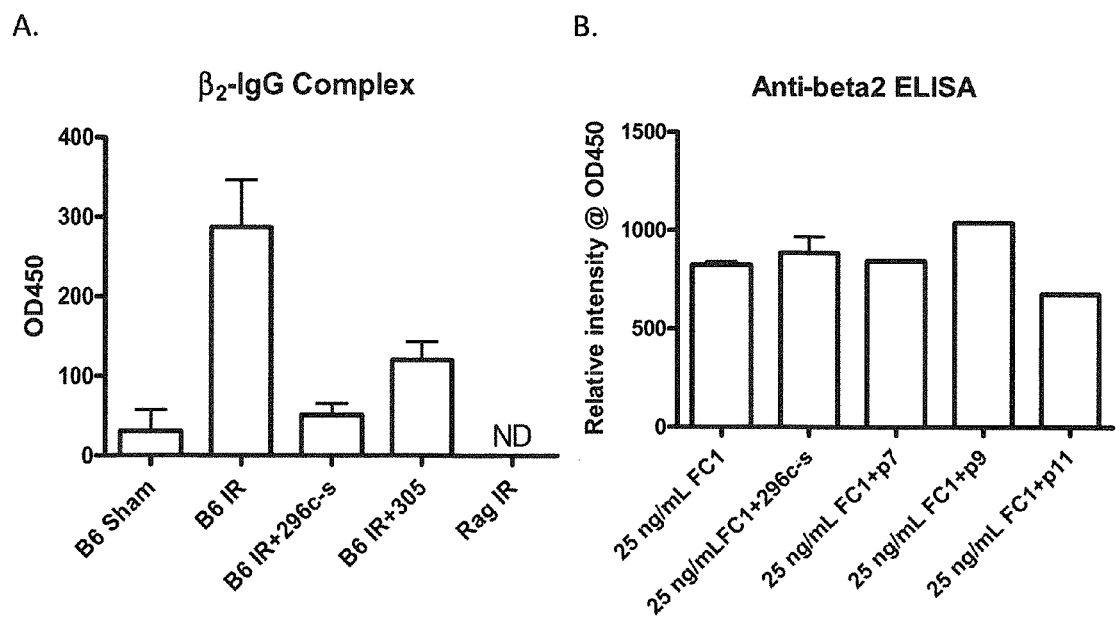
FIG. 27 shows graphs of anti-β2-GPI β2-GPI-IgG complex formation and Ab binding from Example 4.

It was uncertain whether the peptides competed with β2-GPI for binding of anti-β2-GPI Ab. Thus, we analyzed anti-β2-GPI β2-GPI-IgG complex formation and Ab binding in an ELISA. The results are shown in FIG. 27, where each bar represents duplicate samples of a single experiment (FIG. 27(A)). In vivo β2-GPI-IgG complexes are significantly more prevalent after IR in the absence of peptide and either peptide prevents the formation of the complex. In addition, anti-β2-GPI Ab did not bind to peptides alone (data not shown) and peptides did not compete for Ab binding to β2-GPI (FIG. 27(B)). These data correlate with the ex vivo data above suggesting that peptides compete for β2-GPI binding to the cell surface and not with antibody binding. As such, the peptides should also prevent tissue damage in other forms of complement-mediated tissue damage including myocardial infarction, stroke, macular degeneration, ocular vaso-occlusive disease and autoimmune diseases such as Systemic Lupus Erythematosus, and anti-phospholipid syndrome.

14. Discussion

The peptide inhibitors block both intestinal damage and inflammation when administered immediately prior to ischemia, and also subsequent to the ischemic event, in both in vitro and mouse model studies. The present Example extends the results achieved in Examples 1-3 to determine time course and dose responses and additional activities of β2-GPI peptides. We demonstrated that smaller peptides are biologically active, not only when administered prior to ischemia but also when administered during or after the reperfusion event. Additionally, peptide treatment was efficacious at equal molar concentrations up to a 10-fold excess of the circulating native protein concentrations. Hence, administration of the peptides during the reperfusion period extends the clinical relevance to therapeutics, in addition to pretreatments. To our knowledge, this is the first demonstration of β2-GPI-derived peptide efficacy in preventing ischemic injury when administered in a clinically relevant mode. Thus, these peptides may be useful in acute scenarios in addition to planned and routine surgical procedures and organ transplants.

In addition, it was surprisingly found that reversed sequences of D-amino acids maintain activity and actually appear to be more effective. These data indicate that the β2-GPI-derived peptides are clinically relevant and suitable for therapeutic treatment of multiple conditions including, myocardial infarction, stroke, organ transplantation, hemorrhage, and cancer.

Interestingly, the peptides appear to have distinct properties, suggesting that treatment with multiple small peptides may be even more effective than using a single type of peptide. For example, peptides 305 and p9 (encompassed within 305) appear to be more critical for inhibiting the inflammatory response (eicosanoids and neutrophil infiltration), and peptides 296c-s and p7 (within 296c-s) attenuate actual epithelial injury more effectively. Hence, a combination of p7 and p9 may be one example of an optimal therapeutic peptide mixture.

Example 5

Peptoid Synthesis

Peptoids can be synthesized manually using a fritted glass apparatus mounted on an oscillating mixer. The solid-phase synthesis developed by Zuckermann et al. is particularly useful (Proc Nat. Acad. Sci. USA. 89:9367-9371 (1992); J. Am. Chem. Soc. 114:10646-10647 (1992); Proc Nat. Acad. Sci. USA. 95:1517-1522 (1998)). Briefly, Fmoc-substituted Rink amide resin (0.2 mmol) can be reacted with 20% piperidine/DMF (5 mL) for 30 min followed by 3 washes with DMF (5 mL) yielding the free amine. The resin can then be treated two successive times for 30 min with bromoacetic acid (2.0 mmol) and diisopropylcarbodiimide (2.0 mmol) in DMF (5 mL). The resin can then be washed 3× with 5 mL DMF, and treated with a solution of the appropriate N-substituted glycine (8.0 mmol) in DMF (5 mL) for 12 h. The bromoacetic acid and N-substitute glycine addition steps can be repeated until an oligomer of the desired length is obtained. The resin is then washed with DMF (3×5 mL) and dichloromethane (5×5 mL). Cleavage from the resin is achieved using 95:5 TFA/triisopropylsilane (8 mL). Removal of the solvent in vacuo results in a crude oil that can be triturated with cold ether (20 mL). The crude mixture obtained can then be centrifuged, followed by removing the ether by decantation, and purifying the resulting solid by RP-HPLC ($H_2O/CH_3CN$ in 0.1% TFA). If desired, the peptoid products can be isolated by lyophilization and characterized by MALDI TOF/TOF mass spectrometry.

We claim:

1. A β2-glycoprotein I-derived peptide, said peptide being selected from the group consisting of IHFYX$^1$KNKEKKX$^1$SYTVEDAQX$^1$RDGTI, where each X$^1$ is S (SEQ ID NO. 1); KKX$^1$SYTVEDAQX$^1$RDGTIEX$^2$X$^3$X$^4$X$^1$FKEHS, where each X$^1$ is S, X$^2$ is I or V, X$^3$ is P or G, and X$^4$ is R or K (SEQ ID NO. 2); KKSSYTVEDAQS (SEQ ID NO. 3); residues 3-12 of SEQ ID NO. 3; residues 3-12 of SEQ ID NO. 3 with D-amino acids; SQADEVTYSS with D-amino acids (SEQ ID NO. 4); TEDAQX$^1$IDGTIEV, where each X$^1$ is S (SEQ ID NO. 5); KKX$^1$SYTEDAQX$^1$IDGTIEVPKX$^1$FKEHS, where each X$^1$ is S (SEQ ID NO. 7); VSFFX$^1$KNKEKKX$^1$SYTEDAQX$^1$IDGTI, where each X$^1$ is S (SEQ ID NO. 8); IHFYX$^1$KNKEKKX$^1$SYTVEAHX$^1$RDGTI, where each X$^1$ is S (SEQ ID NO. 9); KKSSYTVEAHS (SEQ ID NO. 12); residues 3-11 of SEQ ID NO. 12; residues 3-11 of SEQ ID NO. 12 with D-amino acids; SHAEVTYSS (SEQ ID NO. 13), KKSSYTVEAHSRDGTI (SEQ ID NO. 19), and conservatively modified sequence variants thereof which retain the function of said peptide.

2. A pharmaceutical or veterinary composition comprising a β2-glycoprotein I-derived peptide, said peptide being dissolved or dispersed in a pharmaceutically-acceptable carrier, wherein said peptide is selected from the group consisting of IHFYX$^1$KNKEKKX$^1$SYTVEDAQX$^1$RDGTI, where each X$^1$ is S (SEQ ID NO. 1); KKX$^1$SYTVEDAQX$^1$RDGTIEX$^2$X$^3$X$^4$X$^1$FKEHS, where each X$^1$ is S, X$^2$ is I or V, X$^3$ is P or G, and X$^4$ is R or K (SEQ ID NO. 2); KKSSYTVEDAQS (SEQ ID NO. 3); residues 3-12 of SEQ ID NO. 3; residues 3-12 of SEQ ID NO. 3 with D-amino acids; SQADEVTYSS with D-amino acids (SEQ ID NO. 4); TEDAQX$^1$IDGTIEV, where each X$^1$ is S (SEQ ID NO. 5); KKX$^1$SYTEDAQX$^1$IDGTIEVPKX$^1$FKEHS, where each X$^1$ is S (SEQ ID NO. 7); VSFFX$^1$KNKEKKX$^1$SYTEDAQX$^1$IDGTI, where each X$^1$ is S (SEQ ID NO. 8); IHFYX$^1$KNKEKKX$^1$SYTVEAHX$^1$RDGTI, where each X$^1$ is S (SEQ ID NO. 9); KKSSYTVEAHS (SEQ ID NO. 12); residues 3-11 of SEQ ID NO. 12; residues 3-11 of SEQ ID NO. 12 with D-amino acids; SHAEVTYSS (SEQ ID NO. 13), KKSSYTVEAHSRDGTI (SEQ ID NO. 19), and conservatively modified sequence variants thereof which retain the function of said peptide.

3. The composition of claim 2, said carrier being selected from the group consisting of normal saline, sterile water, phosphate buffered saline, ringers lactate and/or dextrose, dimethyl sulfoxide, ethanol, sugars, milk proteins, gelatin, animal oils, vegetable oils, glycerol, and combinations thereof.

4. The composition of claim 2, wherein said peptide is present in said composition at a concentration of from about 4 µM to about 80 µM.

5. The composition of claim 2, further comprising an additional prophylactic or therapeutic agent dissolved or dispersed in said carrier along with said peptide, wherein said agent is selected from the group consisting of medicines, small molecule drugs, biologics, monoclonal antibodies, vitamins, minerals, and combinations thereof.

6. The composition of claim 2, comprising a combination of two or more different β2-glycoprotein I-derived peptides dissolved or dispersed in said pharmaceutically-acceptable carrier.

7. A β2-glycoprotein I-derived peptide and a label, tag, or targeting moiety attached to the C- or N-terminus of said peptide, said peptide being selected from the group consisting of IHFYX$^1$KNKEKKX$^1$SYTVEDAQX$^1$RDGTI, where each X$^1$ is S (SEQ ID NO. 1); KKX$^1$SYTVEDAQX$^1$RDGTIEX$^2$X$^3$X$^4$X$^1$FKEHS, where each X$^1$ is S, X$^2$ is I or V, X$^3$ is P or G, and X$^4$ is R or K (SEQ ID NO. 2); KKSSYTVEDAQS (SEQ ID NO. 3); residues 3-12 of SEQ ID NO. 3; residues 3-12 of SEQ ID NO. 3 with D-amino acids; SQADEVTYSS with D-amino acids (SEQ ID NO. 4); TEDAQX$^1$IDGTIEV, where each X$^1$ is S (SEQ ID NO. 5); KKX$^1$SYTEDAQX$^1$IDGTIEVPKX$^1$FKEHS, where each X$^1$ is S (SEQ ID NO. 7); VSFFX$^1$KNKEKKX$^1$SYTEDAQX$^1$IDGTI, where each X$^1$ is S (SEQ ID NO. 8); IHFYX$^1$KNKEKKX$^1$SYTVEAHX$^1$RDGTI, where each X$^1$ is S (SEQ ID NO. 9); KKSSYTVEAHS (SEQ ID NO. 12); residues 3-11 of SEQ ID NO. 12; residues 3-11 of SEQ ID NO. 12 with D-amino acids; SHAEVTYSS (SEQ ID NO. 13), KKSSYTVEAHSRDGTI (SEQ ID NO. 19), and conservatively modified sequence variants thereof which retain the function of said peptide.

8. The peptide and attached label, tag, or targeting moiety of claim 7, wherein said moiety is selected from the group consisting of FLAG, polyhistidine, biotin, fluorescent markers, stable isotopes, radioactive isotopes, isotope-labeled amino acids, sugars, polyethylene glycol, covalent crosslinking moieties, toxins, lipids, sterols, and combinations thereof.

9. A pharmaceutical or veterinary composition comprising the B2-glycoprotein I-derived peptide and label, tag, or targeting moiety of claim 7, and a pharmaceutically-acceptable carrier.

10. The composition of claim 9, wherein said moiety is selected from the group consisting of FLAG, polyhistidine, biotin, fluorescent markers, stable isotopes, radioactive isotopes, isotope-labeled amino acids, sugars, polyethylene glycol, covalent crosslinking moieties, toxins, lipids, sterols, and combinations thereof.

* * * * *

SEQUENCE LISTING

```
<160> NUMBER OF SEQ ID NOS: 28

<210> SEQ ID NO 1
<211> LENGTH: 26
<212> TYPE: PRT
<213> ORGANISM: Artificial Sequence
<220> FEATURE:
<223> OTHER INFORMATION: Derivative of human B2-glycoprotein I
<220> FEATURE:
<221> NAME/KEY: MISC_FEATURE
<222> LOCATION: (5)..(5)
<223> OTHER INFORMATION: Xaa is Cys or Ser
<220> FEATURE:
<221> NAME/KEY: MISC_FEATURE
<222> LOCATION: (12)..(12)
<223> OTHER INFORMATION: Xaa is Cys or Ser
<220> FEATURE:
<221> NAME/KEY: MISC_FEATURE
<222> LOCATION: (21)..(21)
<223> OTHER INFORMATION: Xaa is Cys or Ser

<400> SEQUENCE: 1

Ile His Phe Tyr Xaa Lys Asn Lys Glu Lys Lys Xaa Ser Tyr Thr Val
1               5                   10                  15

Glu Asp Ala Gln Xaa Arg Asp Gly Thr Ile
            20                  25

<210> SEQ ID NO 2
<211> LENGTH: 27
<212> TYPE: PRT
<213> ORGANISM: Artificial Sequence
<220> FEATURE:
<223> OTHER INFORMATION: Derivative of human B2-glycoprotein I
<220> FEATURE:
<221> NAME/KEY: MISC_FEATURE
<222> LOCATION: (3)..(3)
<223> OTHER INFORMATION: Xaa is Cys or Ser
<220> FEATURE:
<221> NAME/KEY: MISC_FEATURE
<222> LOCATION: (12)..(12)
<223> OTHER INFORMATION: Xaa is Cys or Ser
<220> FEATURE:
<221> NAME/KEY: MISC_FEATURE
<222> LOCATION: (19)..(19)
<223> OTHER INFORMATION: Xaa is Ile or Val
<220> FEATURE:
<221> NAME/KEY: MISC_FEATURE
```

```
<222> LOCATION: (20)..(20)
<223> OTHER INFORMATION: Xaa is Pro or Gly
<220> FEATURE:
<221> NAME/KEY: MISC_FEATURE
<222> LOCATION: (21)..(21)
<223> OTHER INFORMATION: Xaa is Arg or Lys
<220> FEATURE:
<221> NAME/KEY: MISC_FEATURE
<222> LOCATION: (22)..(22)
<223> OTHER INFORMATION: Xaa is Cys or Ser

<400> SEQUENCE: 2

Lys Lys Xaa Ser Tyr Thr Val Glu Asp Ala Gln Xaa Arg Asp Gly Thr
1               5                   10                  15

Ile Glu Xaa Xaa Xaa Xaa Phe Lys Glu His Ser
            20                  25

<210> SEQ ID NO 3
<211> LENGTH: 12
<212> TYPE: PRT
<213> ORGANISM: Artificial Sequence
<220> FEATURE:
<223> OTHER INFORMATION: Derivative of human B2-glycoprotein I

<400> SEQUENCE: 3

Lys Lys Ser Ser Tyr Thr Val Glu Asp Ala Gln Ser
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Derivative of human B2-glycloprotein I
<220> FEATURE:
<221> NAME/KEY: MISC_FEATURE
<222> LOCATION: (1)..(10)
<223> OTHER INFORMATION: D-amino acids

<400> SEQUENCE: 4

Ser Gln Ala Asp Glu Val Thr Tyr Ser Ser
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Derivative of human B2-glycoprotein I
<220> FEATURE:
<221> NAME/KEY: MISC_FEATURE
<222> LOCATION: (6)..(6)
<223> OTHER INFORMATION: Xaa is Cys or Ser

<400> SEQUENCE: 5

Thr Glu Asp Ala Gln Xaa Ile Asp Gly Thr Ile Glu Val
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Derivative of human B2-glycoprotein I
<220> FEATURE:
<221> NAME/KEY: MISC_FEATURE
<222> LOCATION: (1)..(1)
<223> OTHER INFORMATION: Xaa is Cys or Ser
<220> FEATURE:
<221> NAME/KEY: MISC_FEATURE
```

```
<222> LOCATION: (9)..(9)
<223> OTHER INFORMATION: Xaa is Pro or Gly
<220> FEATURE:
<221> NAME/KEY: MISC_FEATURE
<222> LOCATION: (11)..(11)
<223> OTHER INFORMATION: Xaa is Cys or Ser

<400> SEQUENCE: 6

Xaa Ile Asp Gly Thr Ile Glu Val Xaa Lys Xaa
1               5                   10

<210> SEQ ID NO 7
<211> LENGTH: 26
<212> TYPE: PRT
<213> ORGANISM: Artificial Sequence
<220> FEATURE:
<223> OTHER INFORMATION: Derivative of human B2-glycoprotein I
<220> FEATURE:
<221> NAME/KEY: MISC_FEATURE
<222> LOCATION: (3)..(3)
<223> OTHER INFORMATION: Xaa is Cys or Ser
<220> FEATURE:
<221> NAME/KEY: MISC_FEATURE
<222> LOCATION: (11)..(11)
<223> OTHER INFORMATION: Xaa is Cys or Ser
<220> FEATURE:
<221> NAME/KEY: MISC_FEATURE
<222> LOCATION: (21)..(21)
<223> OTHER INFORMATION: Xaa is Cys or Ser

<400> SEQUENCE: 7

Lys Lys Xaa Ser Tyr Thr Glu Asp Ala Gln Xaa Ile Asp Gly Thr Ile
1               5                   10                  15

Glu Val Pro Lys Xaa Phe Lys Glu His Ser
            20                  25

<210> SEQ ID NO 8
<211> LENGTH: 25
<212> TYPE: PRT
<213> ORGANISM: Artificial Sequence
<220> FEATURE:
<223> OTHER INFORMATION: Derivative of human B2-glycoprotein I
<220> FEATURE:
<221> NAME/KEY: MISC_FEATURE
<222> LOCATION: (5)..(5)
<223> OTHER INFORMATION: Xaa is Cys or Ser
<220> FEATURE:
<221> NAME/KEY: MISC_FEATURE
<222> LOCATION: (12)..(12)
<223> OTHER INFORMATION: Xaa is Cys or Ser
<220> FEATURE:
<221> NAME/KEY: MISC_FEATURE
<222> LOCATION: (20)..(20)
<223> OTHER INFORMATION: Xaa is Cys or Ser

<400> SEQUENCE: 8

Val Ser Phe Phe Xaa Lys Asn Lys Glu Lys Lys Xaa Ser Tyr Thr Glu
1               5                   10                  15

Asp Ala Gln Xaa Ile Asp Gly Thr Ile
            20                  25

<210> SEQ ID NO 9
<211> LENGTH: 25
<212> TYPE: PRT
<213> ORGANISM: Artificial Sequence
<220> FEATURE:
<223> OTHER INFORMATION: Derivative of mouse B2-glycoprotein I
<220> FEATURE:
<221> NAME/KEY: MISC_FEATURE
<222> LOCATION: (5)..(5)
<223> OTHER INFORMATION: Xaa is Cys or Ser
```

```
<220> FEATURE:
<221> NAME/KEY: MISC_FEATURE
<222> LOCATION: (12)..(12)
<223> OTHER INFORMATION: Xaa is Cys or Ser
<220> FEATURE:
<221> NAME/KEY: MISC_FEATURE
<222> LOCATION: (20)..(20)
<223> OTHER INFORMATION: Xaa is Cys or Ser

<400> SEQUENCE: 9

Ile His Phe Tyr Xaa Lys Asn Lys Glu Lys Lys Xaa Ser Tyr Thr Val
1               5                   10                  15

Glu Ala His Xaa Arg Asp Gly Thr Ile
            20                  25

<210> SEQ ID NO 10
<211> LENGTH: 26
<212> TYPE: PRT
<213> ORGANISM: Artificial Sequence
<220> FEATURE:
<223> OTHER INFORMATION: Derivative of mouse B2-glycoprotein I

<400> SEQUENCE: 10

Lys Lys Cys Ser Tyr Thr Val Glu Ala His Cys Arg Asp Gly Thr Ile
1               5                   10                  15

Glu Ile Pro Ser Cys Phe Lys Glu His Ser
            20                  25

<210> SEQ ID NO 11
<211> LENGTH: 7
<212> TYPE: PRT
<213> ORGANISM: Artificial Sequence
<220> FEATURE:
<223> OTHER INFORMATION: Derivative of mouse B2-glycoprotein I

<400> SEQUENCE: 11

Ser Lys Asn Lys Glu Lys Lys
1               5

<210> SEQ ID NO 12
<211> LENGTH: 11
<212> TYPE: PRT
<213> ORGANISM: Artificial Sequence
<220> FEATURE:
<223> OTHER INFORMATION: Derivative of mouse B2-glycoprotein I

<400> SEQUENCE: 12

Lys Lys Ser Ser Tyr Thr Val Glu Ala His Ser
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Derivative of mouse B2-glycoprotein I
<220> FEATURE:
<221> NAME/KEY: MISC_FEATURE
<222> LOCATION: (1)..(9)
<223> OTHER INFORMATION: D-amino acids

<400> SEQUENCE: 13

Ser His Ala Glu Val Thr Tyr Ser Ser
1               5

<210> SEQ ID NO 14
<211> LENGTH: 345
```

```
<212> TYPE: PRT
<213> ORGANISM: Murine

<400> SEQUENCE: 14

Met Val Ser Pro Val Leu Ala Leu Phe Ser Ala Phe Leu Cys His Val
1               5                   10                  15

Ala Ile Ala Gly Arg Ile Cys Pro Lys Pro Asp Asp Leu Pro Phe Ala
            20                  25                  30

Thr Val Val Pro Leu Lys Thr Ser Tyr Asp Pro Gly Glu Gln Ile Val
        35                  40                  45

Tyr Ser Cys Lys Pro Gly Tyr Val Ser Arg Gly Gly Met Arg Arg Phe
    50                  55                  60

Thr Cys Pro Leu Thr Gly Met Trp Pro Ile Asn Thr Leu Arg Cys Val
65                  70                  75                  80

Pro Arg Val Cys Pro Phe Ala Gly Ile Leu Glu Asn Gly Ile Val Arg
                85                  90                  95

Tyr Thr Ser Phe Glu Tyr Pro Lys Asn Ile Ser Phe Ala Cys Asn Pro
            100                 105                 110

Gly Phe Phe Leu Asn Gly Thr Ser Ser Lys Cys Thr Glu Glu Gly
        115                 120                 125

Lys Trp Ser Pro Asp Ile Pro Ala Cys Ala Arg Ile Thr Cys Pro Pro
    130                 135                 140

Pro Pro Val Pro Lys Phe Ala Leu Leu Lys Asp Tyr Arg Pro Ser Ala
145                 150                 155                 160

Gly Asn Asn Ser Leu Tyr Gln Asp Thr Val Val Phe Lys Cys Leu Pro
                165                 170                 175

His Phe Ala Met Ile Gly Asn Asp Thr Val Met Cys Thr Glu Gln Gly
            180                 185                 190

Asn Trp Thr Arg Leu Pro Glu Cys Leu Glu Val Lys Cys Pro Phe Pro
        195                 200                 205

Pro Arg Pro Glu Asn Gly Tyr Val Asn Tyr Pro Ala Lys Pro Val Leu
    210                 215                 220

Leu Tyr Lys Asp Lys Ala Thr Phe Gly Cys His Glu Thr Tyr Lys Leu
225                 230                 235                 240

Asp Gly Pro Glu Glu Ala Glu Cys Thr Lys Thr Gly Thr Trp Ser Phe
                245                 250                 255

Leu Pro Thr Cys Arg Glu Ser Cys Lys Leu Pro Val Lys Lys Ala Thr
            260                 265                 270

Val Leu Tyr Gln Gly Met Arg Val Lys Ile Gln Glu Gln Phe Lys Asn
        275                 280                 285

Gly Met Met His Gly Asp Lys Ile His Phe Tyr Cys Lys Asn Lys Glu
    290                 295                 300

Lys Lys Cys Ser Tyr Thr Val Glu Ala His Cys Arg Asp Gly Thr Ile
305                 310                 315                 320

Glu Ile Pro Ser Cys Phe Lys Glu His Ser Ser Leu Ala Phe Trp Lys
                325                 330                 335

Thr Asp Ala Ser Glu Leu Thr Pro Cys
            340                 345

<210> SEQ ID NO 15
<211> LENGTH: 345
<212> TYPE: PRT
<213> ORGANISM: Homo sapiens

<400> SEQUENCE: 15
```

```
Met Ile Ser Pro Val Leu Ile Leu Phe Ser Phe Leu Cys His Val
1               5                   10                  15

Ala Ile Ala Gly Arg Thr Cys Pro Lys Pro Asp Asp Leu Pro Phe Ser
            20                  25                  30

Thr Val Val Pro Leu Lys Thr Phe Tyr Glu Pro Gly Glu Glu Ile Thr
        35                  40                  45

Tyr Ser Cys Lys Pro Gly Tyr Val Ser Arg Gly Gly Met Arg Lys Phe
    50                  55                  60

Ile Cys Pro Leu Thr Gly Leu Trp Pro Ile Asn Thr Leu Lys Cys Thr
65                  70                  75                  80

Pro Arg Val Cys Pro Phe Ala Gly Ile Leu Glu Asn Gly Ala Val Arg
                85                  90                  95

Tyr Thr Thr Phe Glu Tyr Pro Asn Thr Ile Ser Phe Ser Cys Asn Thr
            100                 105                 110

Gly Phe Tyr Leu Asn Gly Ala Asp Ser Ala Lys Cys Thr Glu Glu Gly
        115                 120                 125

Lys Trp Ser Pro Glu Leu Pro Val Cys Ala Pro Ile Ile Cys Pro Pro
    130                 135                 140

Pro Ser Ile Pro Thr Phe Ala Thr Leu Arg Val Tyr Lys Pro Ser Ala
145                 150                 155                 160

Gly Asn Asn Ser Leu Tyr Arg Asp Thr Ala Val Phe Glu Cys Leu Pro
                165                 170                 175

Gln His Ala Met Phe Gly Asn Asp Thr Ile Thr Cys Thr Thr His Gly
            180                 185                 190

Asn Trp Thr Lys Leu Pro Glu Cys Arg Glu Val Lys Cys Pro Phe Pro
        195                 200                 205

Ser Arg Pro Asp Asn Gly Phe Val Asn Tyr Pro Ala Lys Pro Thr Leu
    210                 215                 220

Tyr Tyr Lys Asp Lys Ala Thr Phe Gly Cys His Asp Gly Tyr Ser Leu
225                 230                 235                 240

Asp Gly Pro Glu Glu Ile Glu Cys Thr Lys Leu Gly Asn Trp Ser Ala
                245                 250                 255

Met Pro Ser Cys Lys Ala Ser Cys Lys Val Pro Val Lys Lys Ala Thr
            260                 265                 270

Val Val Tyr Gln Gly Glu Arg Val Lys Ile Gln Glu Lys Phe Lys Asn
        275                 280                 285

Gly Met Leu His Gly Asp Lys Val Ser Phe Phe Cys Lys Asn Lys Glu
    290                 295                 300

Lys Lys Cys Ser Tyr Thr Glu Asp Ala Gln Cys Ile Asp Gly Thr Ile
305                 310                 315                 320

Glu Val Pro Lys Cys Phe Lys Glu His Ser Ser Leu Ala Phe Trp Lys
                325                 330                 335

Thr Asp Ala Ser Asp Val Lys Pro Cys
            340                 345

<210> SEQ ID NO 16
<211> LENGTH: 15
<212> TYPE: PRT
<213> ORGANISM: Artificial Sequence
<220> FEATURE:
<223> OTHER INFORMATION: Derivative of mouse B2-glycoprotein I

<400> SEQUENCE: 16

Lys Asn Ile Ser Phe Ala Cys Asn Pro Gly Phe Phe Leu Asn Gly
1               5                   10                  15
```

```
<210> SEQ ID NO 17
<211> LENGTH: 12
<212> TYPE: PRT
<213> ORGANISM: Artificial Sequence
<220> FEATURE:
<223> OTHER INFORMATION: Derivative of mouse B2-glycoprotein I

<400> SEQUENCE: 17

Gly Asn Asp Thr Val Met Cys Thr Glu Gln Gln Asn
1               5                   10

<210> SEQ ID NO 18
<211> LENGTH: 24
<212> TYPE: PRT
<213> ORGANISM: Artificial Sequence
<220> FEATURE:
<223> OTHER INFORMATION: Derivative of mouse B2-glycoprotein I

<400> SEQUENCE: 18

Ile Pro Ser Cys Phe Lys Glu His Ser Ser Leu Ala Phe Trp Lys Thr
1               5                   10                  15

Asp Ala Ser Glu Leu Thr Pro Cys
            20

<210> SEQ ID NO 19
<211> LENGTH: 16
<212> TYPE: PRT
<213> ORGANISM: Artificial Sequence
<220> FEATURE:
<223> OTHER INFORMATION: Derivative of mouse B2-glycoprotein I

<400> SEQUENCE: 19

Lys Lys Ser Ser Tyr Thr Val Glu Ala His Ser Arg Asp Gly Thr Ile
1               5                   10                  15

<210> SEQ ID NO 20
<211> LENGTH: 17
<212> TYPE: PRT
<213> ORGANISM: Artificial Sequence
<220> FEATURE:
<223> OTHER INFORMATION: Derivative of mouse B2-glycoprotein I

<400> SEQUENCE: 20

Asp Glu Val His Tyr Thr Thr Ser Ser Ser Lys Lys Ala Arg Gly Ile
1               5                   10                  15

Ile

<210> SEQ ID NO 21
<211> LENGTH: 19
<212> TYPE: DNA
<213> ORGANISM: Artificial Sequence
<220> FEATURE:
<223> OTHER INFORMATION: PCR Primer

<400> SEQUENCE: 21
ggttgatcct gccagtagc                                                19

<210> SEQ ID NO 22
<211> LENGTH: 20
<212> TYPE: DNA
<213> ORGANISM: Artificial Sequence
<220> FEATURE:
<223> OTHER INFORMATION: PCR Primer

<400> SEQUENCE: 22
```

-continued

```
gcgaccaaag gaaccataac                                              20

<210> SEQ ID NO 23
<211> LENGTH: 20
<212> TYPE: DNA
<213> ORGANISM: Artificial Sequence
<220> FEATURE:
<223> OTHER INFORMATION: PCR Primer

<400> SEQUENCE: 23
cttccaagga cagccaagag                                              20

<210> SEQ ID NO 24
<211> LENGTH: 20
<212> TYPE: DNA
<213> ORGANISM: Artificial Sequence
<220> FEATURE:
<223> OTHER INFORMATION: PCR Primer

<400> SEQUENCE: 24
gtggttgcca ttcaagtgtg                                              20

<210> SEQ ID NO 25
<211> LENGTH: 20
<212> TYPE: DNA
<213> ORGANISM: Artificial Sequence
<220> FEATURE:
<223> OTHER INFORMATION: PCR Primer

<400> SEQUENCE: 25
tgctctcgaa gcccagtatt                                              20

<210> SEQ ID NO 26
<211> LENGTH: 20
<212> TYPE: DNA
<213> ORGANISM: Artificial Sequence
<220> FEATURE:
<223> OTHER INFORMATION: PCR Primer

<400> SEQUENCE: 26
tgtgaatgtt gctgggtcat                                              20

<210> SEQ ID NO 27
<211> LENGTH: 20
<212> TYPE: DNA
<213> ORGANISM: Artificial Sequence
<220> FEATURE:
<223> OTHER INFORMATION: PCR Primer

<400> SEQUENCE: 27
agagcaacat caccatgcag                                              20

<210> SEQ ID NO 28
<211> LENGTH: 20
<212> TYPE: DNA
<213> ORGANISM: Artificial Sequence
<220> FEATURE:
<223> OTHER INFORMATION: PCR Primer

<400> SEQUENCE: 28
tttcttgcgc tttcgttttt                                              20
```